(12) United States Patent
Seymour et al.

(10) Patent No.: US 8,195,267 B2
(45) Date of Patent: Jun. 5, 2012

(54) MICROELECTRODE WITH LATERALLY EXTENDING PLATFORM FOR REDUCTION OF TISSUE ENCAPSULATION

(76) Inventors: John P. Seymour, Toledo, OH (US); Daryl R. Kipke, Dexter, MI (US)

(*) Notice: Subject to any disclaimer, the term of this patent is extended or adjusted under 35 U.S.C. 154(b) by 494 days.

(21) Appl. No.: 11/576,321

(22) PCT Filed: Jan. 26, 2007

(86) PCT No.: PCT/US2007/002465
§ 371 (c)(1),
(2), (4) Date: Jul. 31, 2009

(87) PCT Pub. No.: WO2007/089738
PCT Pub. Date: Aug. 9, 2007

(65) Prior Publication Data
US 2009/0299167 A1    Dec. 3, 2009

Related U.S. Application Data

(60) Provisional application No. 60/762,267, filed on Jan. 26, 2006.

(51) Int. Cl.
*A61B 5/04* (2006.01)
*A61N 1/05* (2006.01)
(52) U.S. Cl. .................. 600/377; 600/378; 607/116
(58) Field of Classification Search .............. 600/373, 600/377, 378; 607/116
See application file for complete search history.

(56) References Cited

U.S. PATENT DOCUMENTS

| | | | |
|---|---|---|---|
| 3,847,687 A | 11/1974 | Davidsohn et al. | |
| 3,921,916 A | 11/1975 | Bassous | |
| 4,461,304 A | 7/1984 | Kuperstein | |
| 5,207,709 A | 5/1993 | Picha | |
| 5,215,088 A | 6/1993 | Normann et al. | |
| 5,308,442 A | 5/1994 | Taub et al. | |
| 5,385,635 A | 1/1995 | O'Neill | |
| 5,515,848 A | 5/1996 | Corbett, III et al. | |
| 5,524,338 A | 6/1996 | Martyniuk et al. | |
| 5,585,827 A | 12/1996 | Murakami | |
| 5,588,597 A | 12/1996 | Reinecke et al. | |
| 5,843,150 A | 12/1998 | Dreessen et al. | |
| 5,927,277 A | 7/1999 | Baudino et al. | |
| 5,938,694 A | 8/1999 | Jaraczewski et al. | |
| 5,975,085 A | 11/1999 | Rise | |
| 5,989,445 A | 11/1999 | Wise et al. | |
| 5,992,769 A | 11/1999 | Wise et al. | |
| 6,006,124 A | 12/1999 | Fischell et al. | |

(Continued)

FOREIGN PATENT DOCUMENTS
WO    WO-01/12115 A1    2/2001
(Continued)

OTHER PUBLICATIONS

PCT International Search Report for PCT/US07/02465, 7 pages.
(Continued)

*Primary Examiner* — Lee Cohen
(74) *Attorney, Agent, or Firm* — Rader, Fishman & Grauer PLLC; James F. Kamp

(57) ABSTRACT

In some embodiments, an implantable microelectrode is provided with a shank comprised of a laterally extending platform whose thickness and/or configuration contributes to reduced tissue encapsulation, with at least one electrode site disposed at least partially on or in the laterally extending platform. Novel methods of designing, making, and using an implantable microelectrode or biosensor resulting in reduced tissue encapsulation are also disclosed.

11 Claims, 19 Drawing Sheets

U.S. PATENT DOCUMENTS

| | | | |
|---|---|---|---|
| 6,016,449 | A | 1/2000 | Fischell et al. |
| 6,044,304 | A | 3/2000 | Baudino |
| 6,181,569 | B1 | 1/2001 | Chakravorty |
| 6,205,361 | B1 | 3/2001 | Kuzma et al. |
| 6,228,111 | B1 | 5/2001 | Tormala et al. |
| 6,324,433 | B1 | 11/2001 | Errico |
| 6,374,143 | B1 | 4/2002 | Berrang et al. |
| 6,430,443 | B1 | 8/2002 | Karell |
| 6,600,231 | B2 | 7/2003 | Tominaga |
| 6,618,623 | B1 | 9/2003 | Pless et al. |
| 6,834,200 | B2 | 12/2004 | Moxon et al. |
| 6,878,643 | B2 | 4/2005 | Krulevitch et al. |
| 7,004,948 | B1 | 2/2006 | Pianca et al. |
| 7,006,859 | B1 | 2/2006 | Osorio et al. |
| 7,010,356 | B2 | 3/2006 | Jog et al. |
| 7,011,680 | B2 | 3/2006 | Alt |
| 7,089,059 | B1 | 8/2006 | Pless |
| 7,548,775 | B2 | 6/2009 | Kipke et al. |
| 2002/0198446 | A1 | 12/2002 | Hill et al. |
| 2003/0093129 | A1 | 5/2003 | Nicolelis et al. |
| 2003/0100823 | A1 | 5/2003 | Kipke et al. |
| 2004/0006264 | A1 | 1/2004 | Mojarradi et al. |
| 2004/0102828 | A1 | 5/2004 | Lowry et al. |
| 2004/0106169 | A1 | 6/2004 | Evans |
| 2004/0199235 | A1 | 10/2004 | Younis |
| 2005/0004627 | A1 | 1/2005 | Gibson et al. |
| 2005/0021117 | A1 | 1/2005 | He et al. |
| 2005/0137647 | A1 | 6/2005 | Wallace et al. |
| 2006/0247749 | A1 | 11/2006 | Colvin |
| 2006/0258951 | A1 | 11/2006 | Bleich et al. |
| 2006/0276866 | A1 | 12/2006 | McCreery |
| 2006/0282014 | A1 | 12/2006 | Kipke et al. |
| 2007/0073130 | A1 | 3/2007 | Finch et al. |
| 2007/0123765 | A1 | 5/2007 | Hetke et al. |
| 2007/0135885 | A1 | 6/2007 | Risi |
| 2008/0208283 | A1 | 8/2008 | Vetter et al. |
| 2009/0102068 | A1 | 4/2009 | Pellinen et al. |
| 2009/0118806 | A1 | 5/2009 | Vetter et al. |
| 2009/0132042 | A1 | 5/2009 | Hetke et al. |
| 2009/0187196 | A1 | 7/2009 | Vetter |
| 2009/0234426 | A1 | 9/2009 | Pellinen et al. |
| 2009/0240314 | A1 | 9/2009 | Kong et al. |
| 2009/0248118 | A1 | 10/2009 | Bradley et al. |
| 2009/0253977 | A1 | 10/2009 | Kipke et al. |
| 2009/0299167 | A1 | 12/2009 | Seymour |
| 2009/0312770 | A1 | 12/2009 | Kozai et al. |
| 2010/0030298 | A1 | 2/2010 | Martens et al. |
| 2010/0145422 | A1 | 6/2010 | Seymour et al. |

FOREIGN PATENT DOCUMENTS

| | | |
|---|---|---|
| WO | WO-01/97906 A2 | 12/2001 |
| WO | WO-02/41666 A1 | 5/2002 |
| WO | WO-02/096482 A2 | 12/2002 |
| WO | WO-2008/038208 A2 | 4/2008 |
| WO | WO-2008/072125 A1 | 6/2008 |

OTHER PUBLICATIONS

U.S. Appl. No. 12/848,828, filed Aug. 2, 2010, Anderson.

PCT International Search Report of PCT/US2004/035030, mailed Feb. 21, 2005 (4 pages).

Seymour, John P., Kipke, Daryl R. "Neural probe design for reduced tissue encapsulation in CNS" Biomaterials 28 (2007) 3594-3607, Apr. 5, 2007 (14 pages).

Seymour, John P., Elkasabi, Yaseen M., Chen, Hsien-Yeh, Lahann, Joerg, Kipke, Daryl R., "The insulation performance of reactive parylene films in implantable electronic devices" Biomaterials 30 (2009) 6158-6167, Aug. 22, 2009 (10 pages).

Kaplan, et al., "A Novel Fabrication Method of Capillary Tubes on Quartz for Chemical Analysis Applications" IEEE Proceedings, Micro Electro Mechanical Systems, pp. 63-68, Jan. 25-28, 1994 (6 pages).

Lin, et al., "Silicon Processed Microneedles"; IEEE Journal of Microelectromechanical Systems, vol. 8, No. 1, Mar. 1999, pp. 78-84. (7 pages).

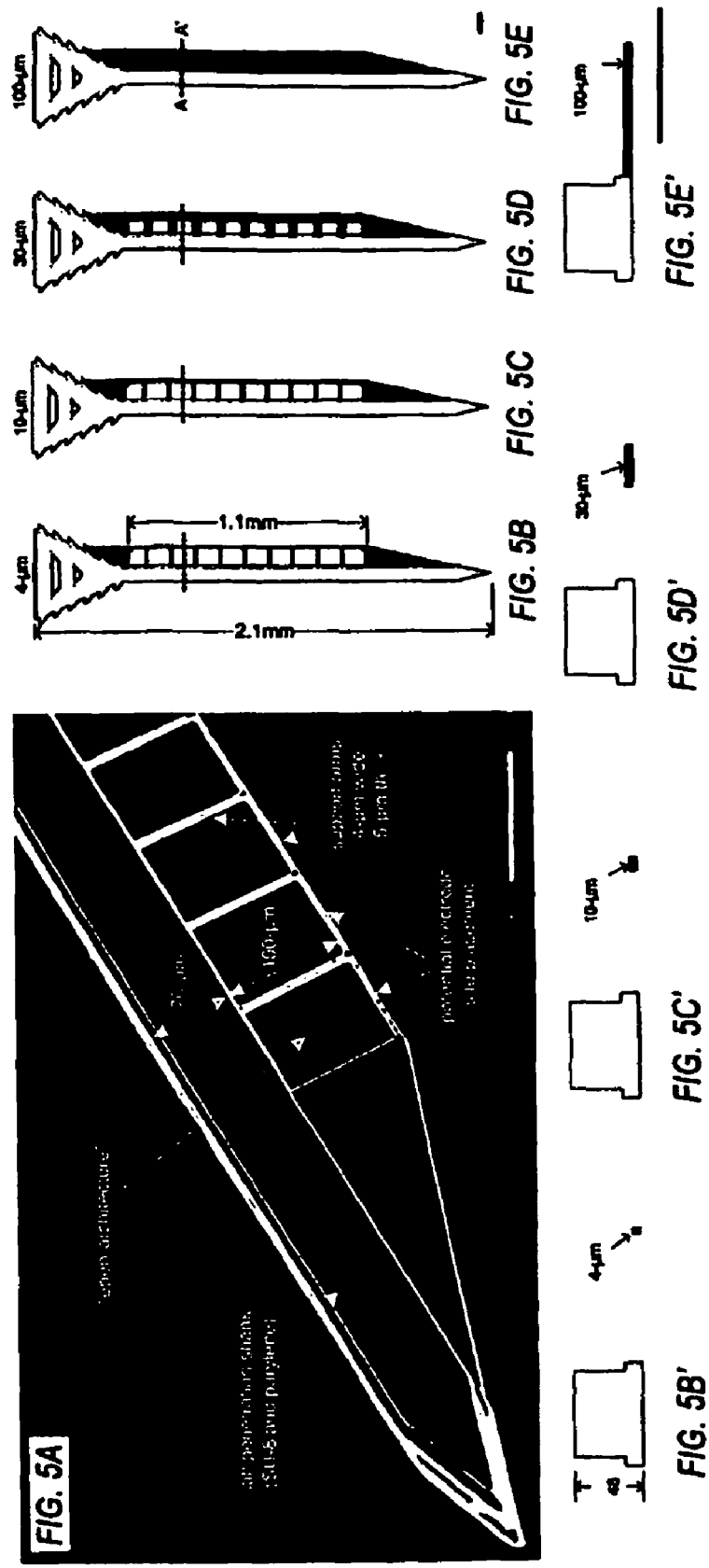

☐ silicon ▦ SiO₂ ■ parylene ■ Ti ■ SU8 ■ 9260

☐ silicon ▨ SiO₂ ■ parylene ■ metal 1 ■ metal 2 ■ metal 3

■ SU8 ■ 9260

MICROELECTRODE WITH LATERALLY EXTENDING PLATFORM FOR REDUCTION OF TISSUE ENCAPSULATION

PRIORITY CLAIM

This application is a National Phase application claiming the benefit of International Application No. PCT/US07/02465, filed Jan. 26, 2007, which claims priority from U.S. Provisional Patent Application Ser. No. 60/762,267, filed Jan. 26, 2006, the complete disclosures of which are each hereby incorporated in full.

STATEMENT REGARDING FEDERALLY SPONSORED RESEARCH OR DEVELOPMENT

This invention was made with government support under EB002030 and NS022346. The government has certain rights in the invention.

FIELD OF THE INVENTION

The present invention relates to the field of implantable microelectrodes.

BACKGROUND

Electrodes on an implantable sensing device are placed into the biological tissue of interest to monitor electrophysiological signals (current or voltage) or chemical/molecular signals (converted into current or voltage), as well as sometimes to deliver stimulating signals. Sensitivity of the electrode over time decreases due to cellular and acellular encapsulation as a result of the foreign body response around the device and electrode.

Recording and/or stimulating microelectrodes can be a critical enabling technology for both neuroscience and prosthetic treatment of spinal cord injury, amyotrophic lateral sclerosis, and limb amputation. Neural prostheses could greatly impact the treatment of these disorders by providing the means to interface the intention of a patient's mind and therefore restore some functional tasks [1-4]. However, the invasive nature of an intracortical neural probe requires high reliability and efficacy standards in order to justify the risk and cost of surgery. Failure due to tissue encapsulation is believed to be a major limitation to their widespread use and is also an issue for many other implantable biosensors [5-7].

Histological examination of intracortical devices has consistently shown that a glial scar forms around the probe tract [8-11]. Cellular components of the glial scar consist of activated microglia and hypertrophied astrocytes, and likely also include meningeal cells [12, 13], foreign body giants [8], and oligodendrocyte precursors [14]. These immunoreactive cells produce extracellular proteins that hinder local nerve regeneration [12, 15]. In addition, a neuronal "kill zone" has been reported around neural implants [11, 16].

After an injury, tissue encapsulation modifies the extracellular space as evidenced by mass transport [5, 17, 18] and impedance spectroscopy studies [19-21]. The injured tissue loses volume fraction and gains tortuosity [22]. Tissue encapsulation is also concomitant with a decrease in the signal quality of neural recordings in the brain and the periphery [19, 21, 23-27]. Wile electrode biofouling also contributes to a loss of performance, tissue encapsulation has been shown to be a large factor [5].

The evidence has motivated the pursuit of several approaches to reduce tissue encapsulation around implantable devices, most notably surface modification [7, 28, 29] and local drug delivery [30-32]. However, a significant unmet need remains for microelectrodes that result in reduced tissue encapsulation and resulting loss of electrode performance.

BRIEF SUMMARY

The present invention was developed in light of these and other drawbacks.

Without limiting the embodiments to only those described in this section, an implantable microelectrode is provided with a shank comprised of a laterally extending platform whose thickness and/or configuration contributes to reduced tissue encapsulation, with at least one electrode site disposed at least partially on or in the laterally extending platform. Novel methods of making and using same are also disclosed.

In some embodiments, without limitation, the invention comprises an implantable microelectrode having a shank and at least one electrode site, wherein the shank comprises a backbone portion and a laterally extending platform, the laterally extending platform having a thickness less than the backbone portion and extending up to about 250 microns radially from the backbone, and wherein at least one electrode site is disposed at least partially on or in the laterally extending platform. In other aspects, such an embodiment may also comprise a laterally extending platform further comprised of at least one longitudinal rib and at least one radially projecting rib projecting from the backbone, wherein the configuration of the longitudinal rib, the radially extending rib, and the backbone form at least one open space in the laterally extending platform. Embodiments also include, without limitation, an implantable microelectrode with a shank comprising a backbone and a laterally extending platform, the laterally extending platform having a thickness of between about 0.5 and 10 microns and less than the backbone portion and extending up to about 250 microns radially from the backbone; one or more electrode; and one or more conductive interconnects disposed between layers of dielectrics in one or both of the shank and the laterally extending platforms the dielectric layers insulating the interconnects on top and bottom sides, wherein the interconnects terminate with respective electrode sites and/or with bond pads and wherein at least one electrode site is disposed at least partially on or in the laterally extending platform.

Other aspects and embodiments of the invention will be apparent to those skilled in the art after reviewing the drawings, detailed description, and claims below.

BRIEF DESCRIPTION OF THE DRAWINGS

The features and inventive aspects of the present invention will become more apparent from the following detailed description, the appended claims, and the accompanying drawings, of which the following is a brief description. Illustrative embodiments are shown in detail. Although the drawings represent some embodiments, the drawings are not necessarily to scale, and certain features may be exaggerated to better illustrate and explain an innovative aspect of an embodiment. Further, the embodiments described herein are not intended to be exhaustive or otherwise limiting or restricting to the precise form and configuration shown in the drawings and disclosed in the following detailed description.

FIG. 5 shows several microelectrode designs with subcellular dimensions.

DETAILED DESCRIPTION

We have discovered unexpectedly that the geometry of an implantable microelectrode can reduce long-term encapsulation by incorporating as some of its aspects subcellular dimensions. Specifically, in some embodiments, we have invented an implantable microelectrode having a penetrating shank comprised of a laterally extending platform ("LEP") extending from the backbone of the shank, where at least portions of the LEP have a thickness of subcellular dimensions. We have discovered unexpectedly that thickness of the LEP is a significant factor in reducing encapsulation around at least the edge of the LEP. In accordance with some aspects, the invention comprises a design of an implantable microelectrode that reduces encapsulation due to the foreign body response and thereby improves long-term efficacy in vivo.

In accordance with our unexpected discovery, in some embodiments, without limitation, the invention comprises an implantable microelectrode which is further comprised of a head and a shank. The shank extends from a distal portion of the head and ends in a tip. The shape of the tip may be chisel, conical, frusto-conical, or any shape suitable to facilitate implantation of the device into biological tissue.

The shank is further comprised of a backbone portion and an LEP. In some embodiments, the thickness of the LEP is less than the thickness of the backbone portion.

In some embodiments, the LEP is comprised of one or more longitudinal ribs that join to one or more radially projecting ribs which extend from the backbone portion of the shank. The configuration of the backbone section of the shank, the longitudinal rib, and the radially projecting ribs form open spaces within the LEP, thus resulting in an open architecture of a "lattice" type in at least some portion of the microelectrode of this embodiment.

In some embodiments, the invention further comprises a microelectrode having an LEP with one or more electrode sites disposed on the LEP. The electrode sites can be recording electrodes, stimulating electrodes, or any configuration or combination thereof. Such embodiments comprises planar or non-planar substrates with a plurality of electrode channels suitable for recording an electrical signal from a cell and/or delivering a stimulating electrical signal to a target site. Some embodiments further comprise interface connectors and cables for connecting the electrodes to non-integrated units such as data acquisition (implantable or external) as part of a chronic monitoring setup for clinical treatment, an electrophysiology study, or chemical sensing.

Figure 1:
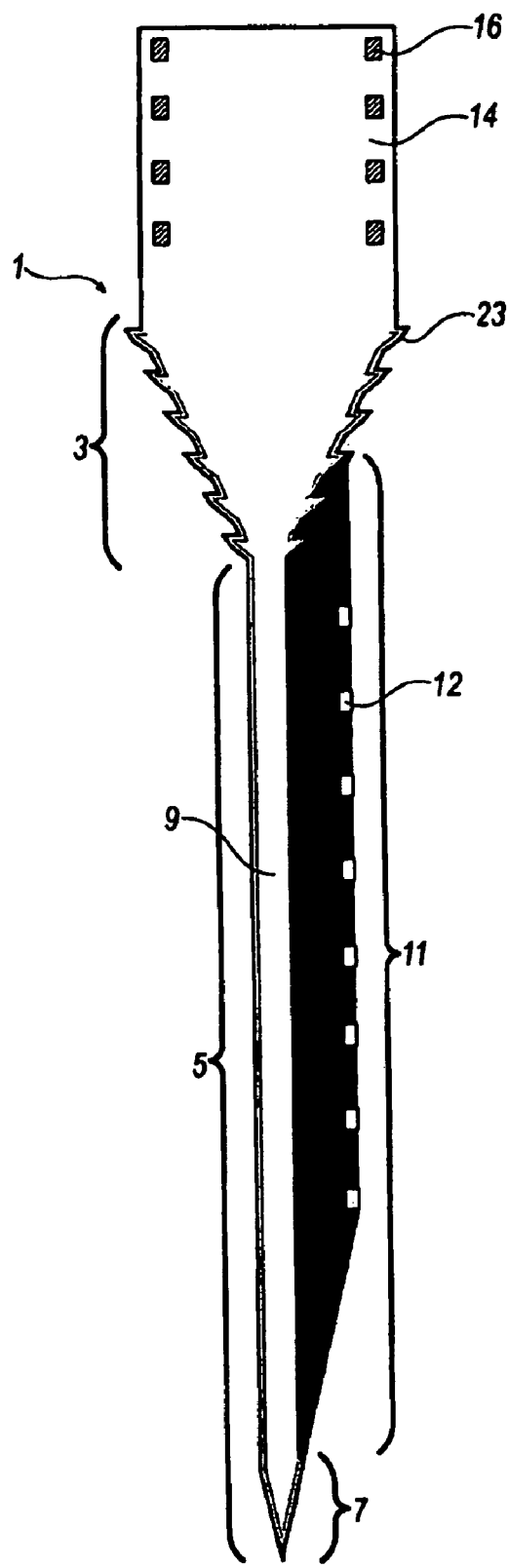
FIG. 1 is a front view of a microelectrode in accordance with one embodiment of the invention.

Without limiting the invention to only those embodiments specifically described herein, FIG. 1 shows aspects of one embodiment of the invention. An implantable microelectrode 1 is comprised of a head 3 that connects at a distal end to a shank 5. Optionally the head 3 may have projections 23 that allow gripping of the head and/or improve retention of the microelectrode 1 in the target implant area.

A distal portion of the shank 5 may be configured to form a tapered tip 7 for ease of insertion. The shank 5 is further comprised of a backbone portion 9 and an LEP portion 11 that extends radially from the backbone portion 9. The backbone portion 9 has greater thickness than the LEP portion and provides increased stiffness and/or thickness for mechanical strength within the microelectrode 1. Stiffness may be provided with inherent material Young's modulus or with appropriate material thickness.

In some embodiments, a portion of the LOP may extend proximally and attach to a portion of the head 3, as shown in FIG. 1.

Figure 2:
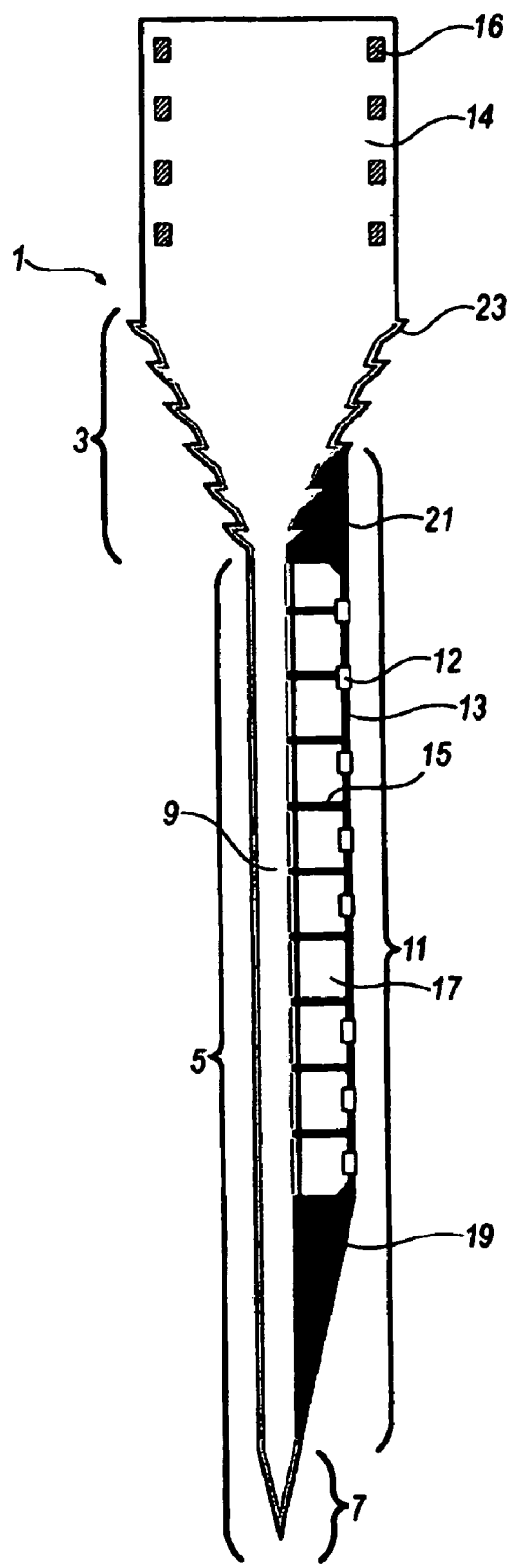
FIG. 2 is a front view of a microelectrode in accordance with another embodiment of the invention, showing a laterally extending platform with open architecture.

As shown in the embodiment of FIG. 2, the LEP portion 11 may be comprised of one or more longitudinal ribs 13 displaced laterally from the backbone portion 9 and a plurality of radially projecting ribs 15 that project outwardly from the backbone portion 9 at any desired angle. The configuration of the backbone portion 9, the longitudinal rib 13, and the radially projecting ribs 15 produces open space 17 of a "lattice" type in the LEP portion 11, thus reducing the surface area of the microelectrode 1 in contact with biological tissue in the targeted implant area (not shown), while also facilitating the incorporation of the LEP portion in the tissue.

Optionally, in some embodiments of a "lattice" configuration, the LEP portion may be comprised of a distal filled section 19 and/or a proximal filled section 21 to facilitate insertion of the microelectrode 1 and/or to add mechanical strength to the lattice portion. In some embodiments, a portion of the LEP 11, for example, a portion of the proximal filled section 21, may extend past the proximal end of the shank and be joined to the head 3, as shown in the embodiment of FIG. 2.

Figure 3A:
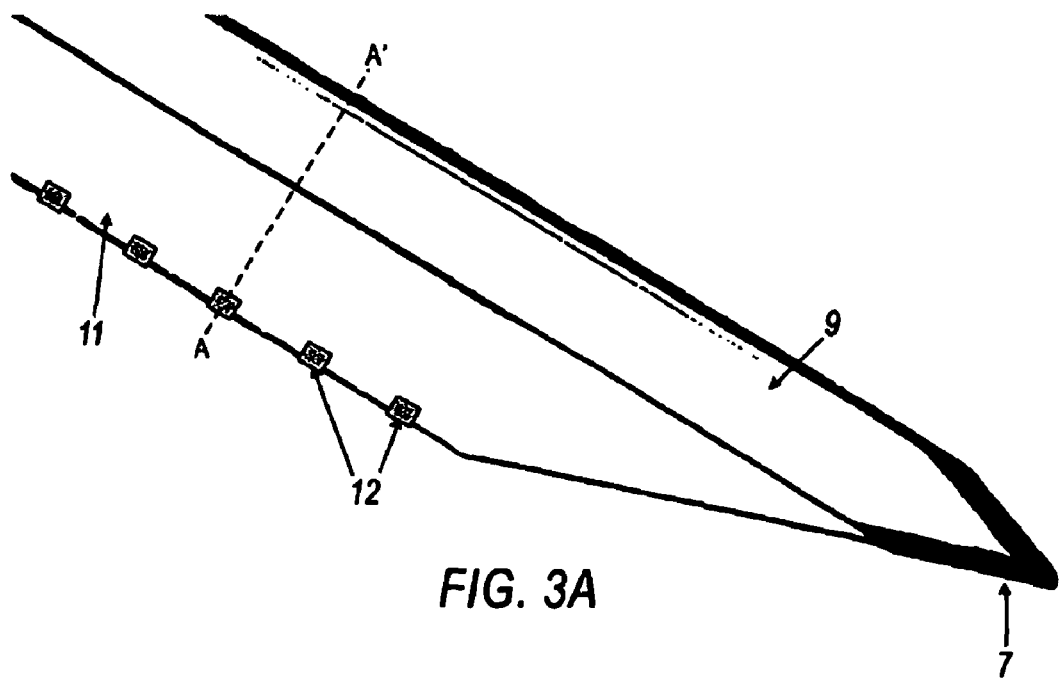
FIG. 3 is an illustrative drawing of an microelectrode according to some aspects of the invention.
Figure 3B:
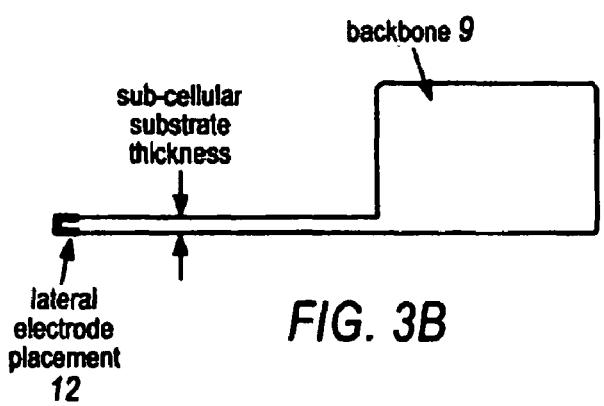
Figure 3C:
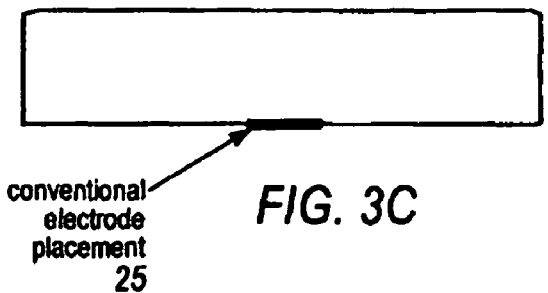

As shown variously in FIGS. 1-3, in some embodiments, one or more electrode sites 12 are disposed at least partially on or in the LEP 11. FIG. 1 shows electrode sites 12 disposed on or in the LEP 11. FIG. 2 shows electrodes sites disposed on or in a longitudinal rib portion 13 of an LEP 11. FIG. 3 shows aspects of one embodiment of the invention comprising an LEP 11, with a plurality of electrode sites 12 disposed on the LEP's most lateral edge where it is generally the thinnest, as one example only, in some embodiments, specifically, less than about 10 microns in thickness. FIG. 3(A) shows an isometric view of the tip of a probe 1 and LEP 11. Multiple electrode sites are visible along the edge of the device whose thickness (see label) is sub-cellular or less than 10 microns. FIG. 3(B) shows a cross-sectional view through A-A'. The sample cross-section shows exemplary electrode site placement to maximize sensitivity. FIG. 3(C) shows cross-sectional view through a conventional planar microelectrode array 25 and conventional electrode site placement. As indicated generally in FIG. 3(B), the backbone portion 9 of the microelectrode 1 is thicker and therefore stiffer that the longitudinal rib 13 or planar LEP 11 containing the electrode sites.

Microelectrodes made in accordance with aspects of the invention can be any suitable length, although lengths between about 0.5 mm and 75 mm are preferred (species dependent). In similar fashion, the backbone portion of the shank may be any suitable width and thickness, although widths of between about 5 and 500 microns and thicknesses between about 11 and 500 microns are preferred. The LEP portion of the shank may extend radially up to about 250 microns from the backbone portion and may be any suitable thickness, although a thickness of between about 0.5 and 10 microns and less than the thickness of the backbone portion is preferred. Similarly, the width of the longitudinal ribs 13 and/or radially projecting ribs, where found, may be any suitable width.

The microelectrode may be comprised of any suitable materials known to those of ordinary skill in the art. As some examples only, such materials may include, individually or in any combination, SU-8, polyimide, parylene, or silicon-based substrates of sufficient Young's modulus or thickness.

Figure 4:
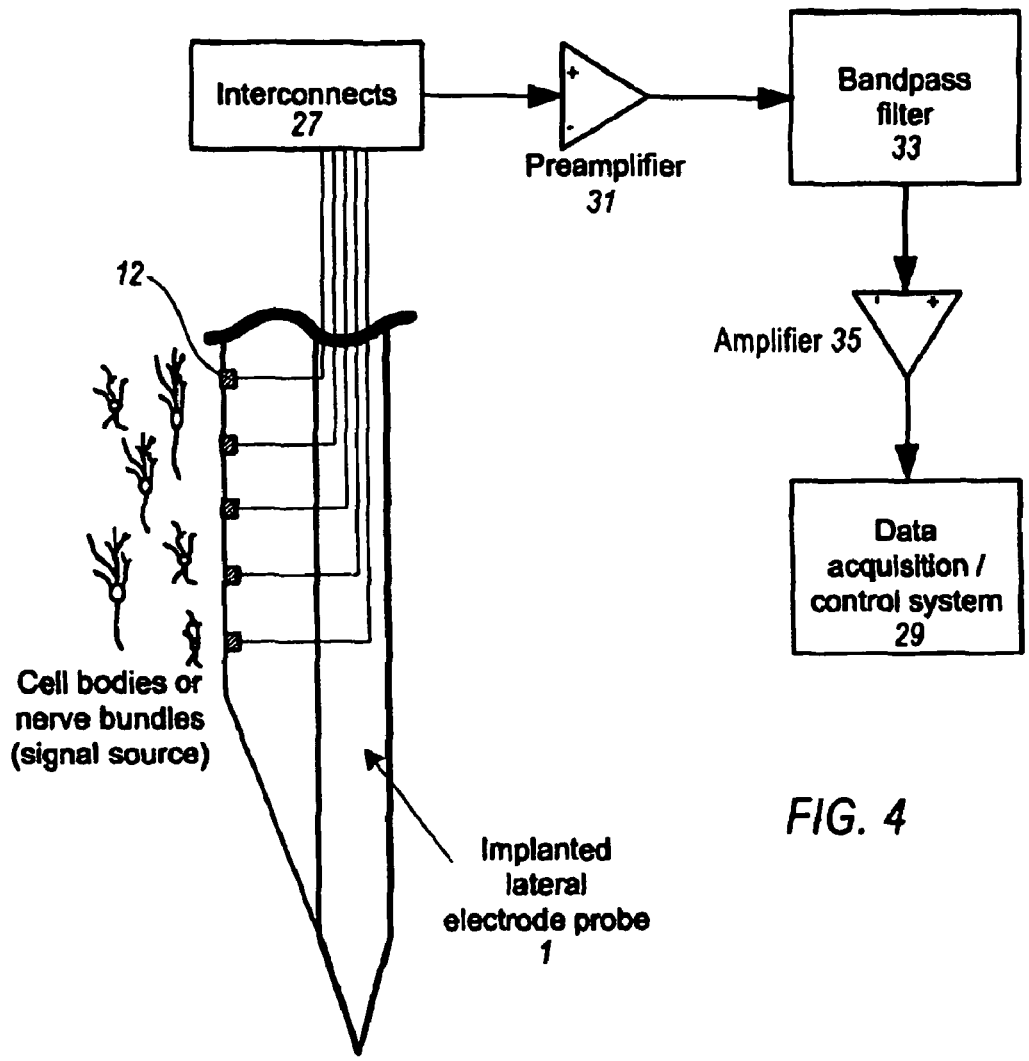
FIG. 4 shows a microelectrode in accordance with one embodiment that was implanted into central nervous tissue and which is in communication with a data acquisition system.
Figure 6A:
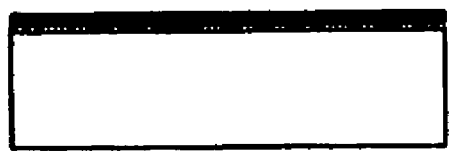
FIGS. 6 and 7 are cross-sectional views of microelectrodes fabricated using a polymer substrate.
Figure 6B:
Figure 6C:
Figure 6D:
Figure 6E:
Figure 6F:
Figure 7A:
Figure 7B:
Figure 7C:
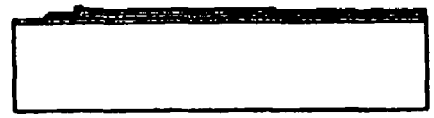
Figure 7D:
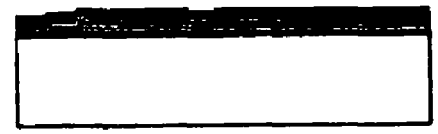
Figure 7E:
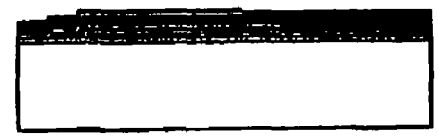
Figure 7F:
Figure 7G:
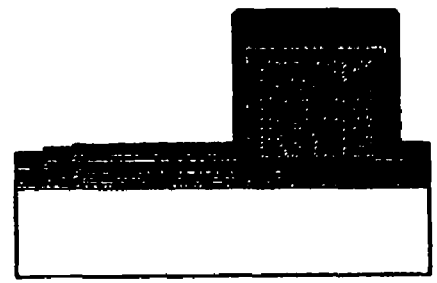
Figure 7H:

Without limitation, FIGS. 1, 2, and 4 show some embodiments with some connecting aspects. As only one example, FIGS. 1 and 2 show bond pads 16 in conjunction with an interconnect region 14. As shown in FIG. 4, without limitation, in some embodiments, the microelectrode comprises a plurality of electrode sites connected to interconnects 27, which run through the body of the microelectrode and can be connected externally to nonintegrated components, such as a computerized data acquisition and control system 29 for signal and data generation and acquisition purposes, and/or any other suitable purposes.

In some embodiments, the electrode sites comprise one or more metal traces disposed within the microelectrode which terminate through via and dielectrics to form an electrode site. Methods of making electrode sites and related connections and tracing are known to those of ordinary skill in the art, for example, see International Publication No. WO2006/138358, which is hereby incorporated in its entirety. In some embodiments, a microelectrode 1 is comprised of conductive interconnects disposed within the microelectrode between layers of dielectrics which insulate the interconnects on top and bottom sides. At least some interconnects terminate with recording and/or stimulation electrode sites 12 and/or with bond pads (not shown) for electrical connection to external instrumentation and/or hybrid chips on the proximal end. In one embodiment, the interconnects are metal (e.g. platinum, gold) and the dielectric is a polymer (e.g. polyimide, parylene, PDMS). In another embodiment, the interconnects are polysilicon insulated with inorganic dielectrics (e.g. $SiO_2$, $Si_3N_4$) and polymer. In another embodiment, the interconnects are polysilicon insulated with inorganic dielectrics that are supported below by a silicon substrate. In yet another embodiment, the device is either a silicon or polymer-based structure with electrode sites, interconnects and bond pads as described above, Electrode sites and bond pads can be formed by opening apertures through the top dielectric and depositing and patterning metal (e.g. iridium, platinum, gold). In one embodiment, at least one of the electrode sites 12, for example, can be larger in area and used as a reference site for recording and/or stimulation. The precision, consistency, and reproducibility of the electrode sites on the microelectrode array result in predictable electrical and spatial characteristics. These characteristics enable the sites to be grouped in a manner that enables precise, predictable, and selective tuning of neural interface regions. Some embodiments of the invention comprise two or more electrode sites grouped to form a larger composite site that enables tuning the neural interface region for recording and/or stimulation. This grouping of sites can be through intrinsic connection of the site traces, or it can be through external connections for 'on the fly' tuning.

As some examples only, an electrode site may be disposed on the top or bottom side within any portion being within about 5 microns of the lateral edge of an LEP or with its most lateral edge substantially flush with the lateral edge of the LEP; the electrode site may be wholly or partially integrated within the thickness of the LEP; and/or the electrode site may wrap around at least portions of the top, side, and/or bottom edges of the LEP. In some embodiments, systems incorporating the microelectrode may include a preamplifier 31, filter 33, and amplifier 35, or any combination of these or other useful components.

EXAMPLE

The following example of some embodiments of the invention is provided without limiting the invention to only those embodiments described herein.

We conducted a study to determine whether tissue encapsulation at the device-tissue interface could be modulated based on probe geometry. Neural probes were developed and tested that had conventional penetrating shanks combined with several types of narrow and wide lattice elements, Encapsulation and neuronal loss were correlated with the different device geometries by employing high resolution confocal images to determine neuronal and nonneuronal cell densities, Double labeling with a variety of immunostains around the intact neural probe provided additional qualitative analysis of the device-tissue microenvironment, including neurons, astrocytes, microglia and several extracellular matrix proteins.

Materials and Methods

Neural Probe Design and Fabrication

A scanning electro microscope ("SEM") image and CAD layout of a lattice-like neural microelectrode with subcellular features is shown in FIG. 5. FIG. 5 is an SEM perspective view of a parylene-based open-architecture device used for in vivo testing, The tip of the device is at the lower left, FIG. 5(b-d) are CAD drawings of various microelectrode designs indicating overall length and width of three lattice structures (4 μm, 10 μm, 30 μm), and FIG. 5(e) shows one non-lattice structure (100 μm wide). FIG. 5(b'-e') Cross-sectional view of line A-A' shown in (b-e). All probes had identical shank and outer dimensions (scale bars=100 μm).

Our study tested four different structures, one without a lattice and three with a lattice design of varying size (FIG. 5(*b-e*)). The shank dimensions were chosen to provide sufficient stiffness to penetrate the rat pia matter. To limit the number of variables, each probe had identical outer dimensions and thus each probe had an identical footprint. Each thin, lateral structure extended 100 µm and was 5 µm thick. Lattice size (4, 10, 30 µm, and 100 µm, the last being solid) and the percentage of open area was unique to each.

The devices were microfabricated in a conventional clean room environment. A sacrificial release layer of SiO2 was grown on a 4-inch silicon wafer. FIG. 6 is a cross-sectional view of a microelectrode in accordance with some embodiments that was fabricated using a polymer substrate. This is a structural embodiment only (FIG. 6): (A) Parylene-C was deposited (5-µm thick) via chemical vapor deposition using a PDS-2010 obtained from Specialty Coating (Indianapolis, Ind.). (B) A Ti layer 1000' was deposited and patterned for later use as a mask for the subcellular lattice structure. (C) SU-8 2025 (Microchem, Newton, Mass.) was spin-coated to 38-µm (±2-µm) and patterned to create the core of the probe shank. Oxygen plasma RIE surface treatment was applied before and after the SU-8 layer to improve interfacial adhesion. (D) The second parylene layer was deposited 5-µm thick. This film conformed to the SU-8 backbone. (E) We spun an 80-µm thick AZ-9260 resist layer to cover the SU-8 structures and mask the shank of the probe. (F) Parylene was etched using oxygen plasma RIE. Devices were released using hydrofluoric acid and then thoroughly rinsed in DI water, ethanol, and acetone. In addition to this purely structural embodiment, which was tested in vivo, FIG. 7 shows a similar structure including the necessary fabrication steps to incorporate the electrodes and interconnects: (A) Parylene deposited on SiO2 sacrificial layer. Pattern parylene mask and etch parylene. (B) Metal 1 deposition and pattern. (C) Metal 2 lift-off (D) Parylene deposition. (E) Metal 3 deposition to create etch stop for thin polymer structure. (F) SU-8 patterned shank and final parylene to encapsulate SU-8 structure. (G) 9260 resist patterned to form thick mask over shank. (H) Etched and released cross-section. Six masks used for photolithography in (A,E,C,E,F,G) in this one embodiment of the invention.

Probe Assembly

A stereotaxic frame was used to insert each probe with a controlled trajectory to minimize insertion damage and variability [16, 38]. First a metal insertion plate (custom machined) placed on a glass slide is heated to ~50° C., and then the glass slide was placed on a dissecting microscope. The probe head was mounted in the notched region of the heated insertion plate using poly(ethylene glycol) or PEG (8000 M.W., Acros, Geel, Belgium). Rapid cooling prevented the PEG from wicking onto the shank of the probe.

The PEG and insertion plate were autoclaved separately prior to assembly. Probes were cleaned before and after assembly with 90% ethanol. Additionally, the probe and insertion plate assembly were sterilized with ethylene oxide (EtO) at ambient temperature and allowed to vent for 24 hours under vacuum. When EtO sterilization was unavailable, ultraviolet exposure in a sterile hood for 30 minutes was used instead.

Surgical Procedure

Multiple devices were surgically implanted in male Sprague Dawley rats (300-350 grams). Anesthesia was administered using intra-peritoneal injections of a mixture of ketamine, xylazine, and acepromazine. The craniotomy spanned approximately 4 mm in the anterior-posterior direction, and 3 mm in the medial-lateral direction and was centered over the M1 and M2 motor cortex. A ~3× stereoscope was used to ensure a nearly orthogonal trajectory and avoid any visible blood vessels. After the device was inserted via the stereotaxic drive, sterile artificial cerebral spinal fluid (Harvard Apparatus, Holliston, Mass.) was added to the craniotomy to release the probe from the insertion plate. By rotating the insertion plate and applying pressure to the probe head (height is 320-µm), the implant was then driven nearly flush with the brain surface to reduce transcranial tethering [13]. Less than 200-µm of the implant was above the brain surface. Four probe types (FIG. 5(*b-e*)) were inserted in random order and orientation. One craniotomy contained all four implants, separated by a minimum of 0.5-mm. Surgical closure included a thin layer of purified calcium alginate followed by silicone and dental acrylic (Co-Oral-Ite Dental Mfg. Co., Diamond Springs, Calif.) [39]. All procedures strictly complied with the United States Department of Agriculture guidelines for the care and use of laboratory animals and were approved by the University of Michigan Animal Care and Use Committee.

Immunohistochemistry

Four weeks after implantation animals were terminally anesthetized. Transcardial perfusion with 100 mL of chilled PBS was followed by 450 mL of 4% (w/v) paraformaldehyde in PBS. The brain tissue was removed and immediately explanted and postfixed overnight in 4% paraformaldehyde. Following postfixation, brain tissue was equilibrated in 30% sucrose in PBS and sectioned at 12-µm on a cryostat.

Tissue sections between cortical layers II and V were immunostained for each marker combination (see Tables 1, 2) spanning approximately 1.1 mm of the cerebral cortex. The depth of interest was easily identified by the probe geometry seen in the transverse sections (see FIG. 5(*b'-d'*)). Sections were not excluded or included based on the presence of a support arm. Sections were treated for 1 hour with blocking solution at room temperature, All antibodies were diluted in blocking solution consisting of 4% (v/v) normal goat serum and 0.3% (v/v) Triton-X-100 for 6-10 hours at room temperature. Alexa-488 and Alexa-568 labeled secondary antibodies (Invitrogen, Carlsbad, Calif.) were diluted in blocking solution to a concentration of 10 µg/mL. Secondary antibodies were incubated for 2 hours at room temperature, All sections were counterstained with 2 µg/mL Hoechst 33342 (Invitrogen) for 10 minutes. After washing with PBS, sections were mounted with a coverglass using the antifade reagent Prolong Gold (Invitrogen).

TABLE 1

Summary of Antibodies

| Antibody | Antigen | Cell (types) | Isotype | Dilution | Vendor |
|---|---|---|---|---|---|
| GFAP | Glial fibrillary acidic | Astrocytes | IgG (rabbit) | 1:400 | Sigma |
| Fibronectin | Fibronectin | Fibroblasts | AI (rabbit) | 1:800 | Sigma |
| Laminin | Laminin | — | AI (rabbit) | 1:400 | Sigma |

TABLE 1-continued

Summary of Antibodies

| Antibody | Antigen | Cell (types) | Isotype | Dilution | Vendor |
| --- | --- | --- | --- | --- | --- |
| NeuN | Neuronal nuclei | Neurons | IgG1 (mouse) | 1:1000 | Chemicon |
| Neurofilament | NF-M intermediate filaments | Neurons | NA (rabbit) | 1:1000 | Novus |
| OX-42 | CR3 on cd11b integrin | Microglia, macrophages | IgG2a (Mouse) | 1:200 | Serotec |

AI = affinity isolated,
NA = not applicable

TABLE 2

Double Label Combinations

| Double Label | Number of Animals | Minimum number of sections per animal |
| --- | --- | --- |
| OX-42, GFAP | 3 | 12 |
| NeuN. GFAP | 7 | 8 |
| NeuN. Laminin | 7 | 8 |
| OX-42, Fibronectin | 7 | 3 |
| NeuN. Neurofilament | 3 | 4 |

Hoechst counterstain used with all

Cell Counting and Statistical Analysis

Figure 8:
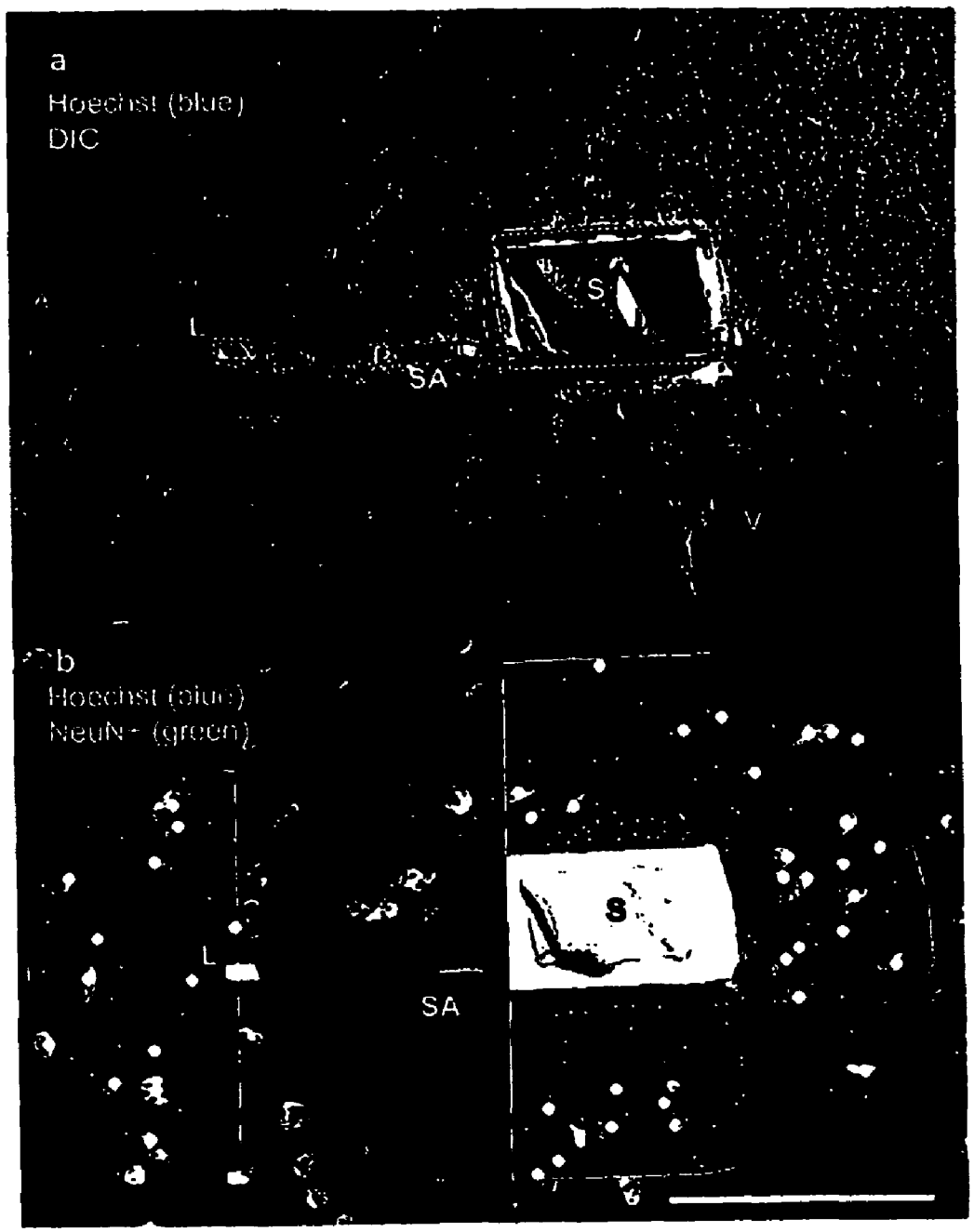
FIG. 8 shows sample images illustrating a counting method.

Eight transverse tissue sections spanning the length of the probe lattice structure (1.1 mm) were randomly chosen for cell counting Confocal images were collected for these NeuN and Hoechst labeled sections using an Olympus FV500 (40×, oil immersion, NA=1.3). A MatLAS graphical user interface was developed for off-line cell selection. First an outline of the intact probe or tissue/device interface was defined by a combination of a differential interference contrast (DIC) and TV fluorescence image (FIG. 8(a). FIG. 8 shows sample images that illustrate the counting methods: FIG. 8(a) Hoechst and differential interference contrast (DIC) image (4-μm probe) used to define the tissue-device interface, showing both lateral edge (L) and probe shank (S). This transverse section has a similar cross-section as shown in FIG. 5(b'). Portion of support arm (SA) was captured in section, as well as large vessel (V). FIG. 8(b) is a screen shot of technician-interface illustrating counting method. Red and yellow dots indicate selection of nonneuronal (Hoechst+, NeuN−) and neuronal cells (NeuN+) respectively. White borders are generated automatically and mark the 75-μm radius from the tissue-device boundary defined in FIG. 8(a). Left and right semi-circular regions represent the lateral edge (L) and probe shank (S) response regions. (Scale-100 μm. 40×Obj.) Small void spaces occasionally present between the implant and tissue as a result of tissue processing were included within the tissue/device interface boundary. A technician (blinded from study) selected all nuclei as either neuronal (NeuN+, Hoechst+) or nonneuronal (Hoechst+ only) from defined regions (lateral edge or probe shank). The two regions were bounded with a radius of 75-μm from the device-tissue boundary (FIG. 8(b)). The probe shank region only included the three outside faces in order to avoid overlap with the lateral edge region. The lateral edge region also included the three outside faces, but only the first 5 μm from the lateral-most point—regardless of the lattice feature size (4, 10, 30, 100 μm). This rule ensured that all regions of interest were equidistant from one another.

After cell selection, the cell coordinates and device-tissue boundary coordinates were stored. A software algorithm used the center of each nucleus (user-selected) to calculate the shortest distance to the device boundary, bin the counts by distance and region, and calculate the sampling area of each bin to form the processed data set.

Each count by bin and region (lateral edge or probe shank) was converted to density using area, Bach density value was normalized by the mean contralateral density to produce unit-less values. Contralateral tissue images were identically processed using the cell selection user-interface and a generic device-tissue boundary overlay. Cells beneath the overlay were not counted. The neuron to nonneuron ratio was a count of neurons (NeuN+) divided by nonneurons (Hoescht+ only). We abbreviate this ratio as N/NN and it was calculated using the original counts.

The test for significance was a two-sided paired t-test (significance threshold of $p<0.05$) using either an N of 7 animals or 28 probes (individual section counts were not used for any portion of the analysis).

Results

Seven male Sprague Dawley rats (300-350 grams) were implanted with the four types of probes described above (FIG. 5(b-e)). There were no mechanical failures during insertion of these 28 devices. Dimpling rarely occurred during insertion. When dimpling did occur (possibly due to the presence of blood vessels near the pial surface [40]), the mild depression did not produce excessive bleeding. High resolution images of the intact probes (transverse cryosections) revealed structural integrity out to 4-weeks post implant (FIG. 8(a)).

The empirical mechanical testing conducted indicated that the tip angle, shank stiffness, and leading edge were sufficiently designed to pierce the rat neocortex in a straight trajectory and prevent damage to the fine 4-μm×5-μm×100-μm parylpene lattice. Larger lattice structures also maintained their integrity. All of the probes had similar tip shapes (13 degrees, chisel-shaped) and outer dimensions. Probe shank dimensions were 68.0±1.1 μm wide by 48.2±2.5 μm thick. The lattice width was 4.0±0.2, 9.8±0.4, and 29.5±0.5 μm respectively.

Quantitative Cell Density as a Function of Device Geometry

Figure 10:
FIG. 10 are IHC images showing NeuN+ reactivity (green) and Hoechst counterstain (blue) for each probe type.
Figure 11:
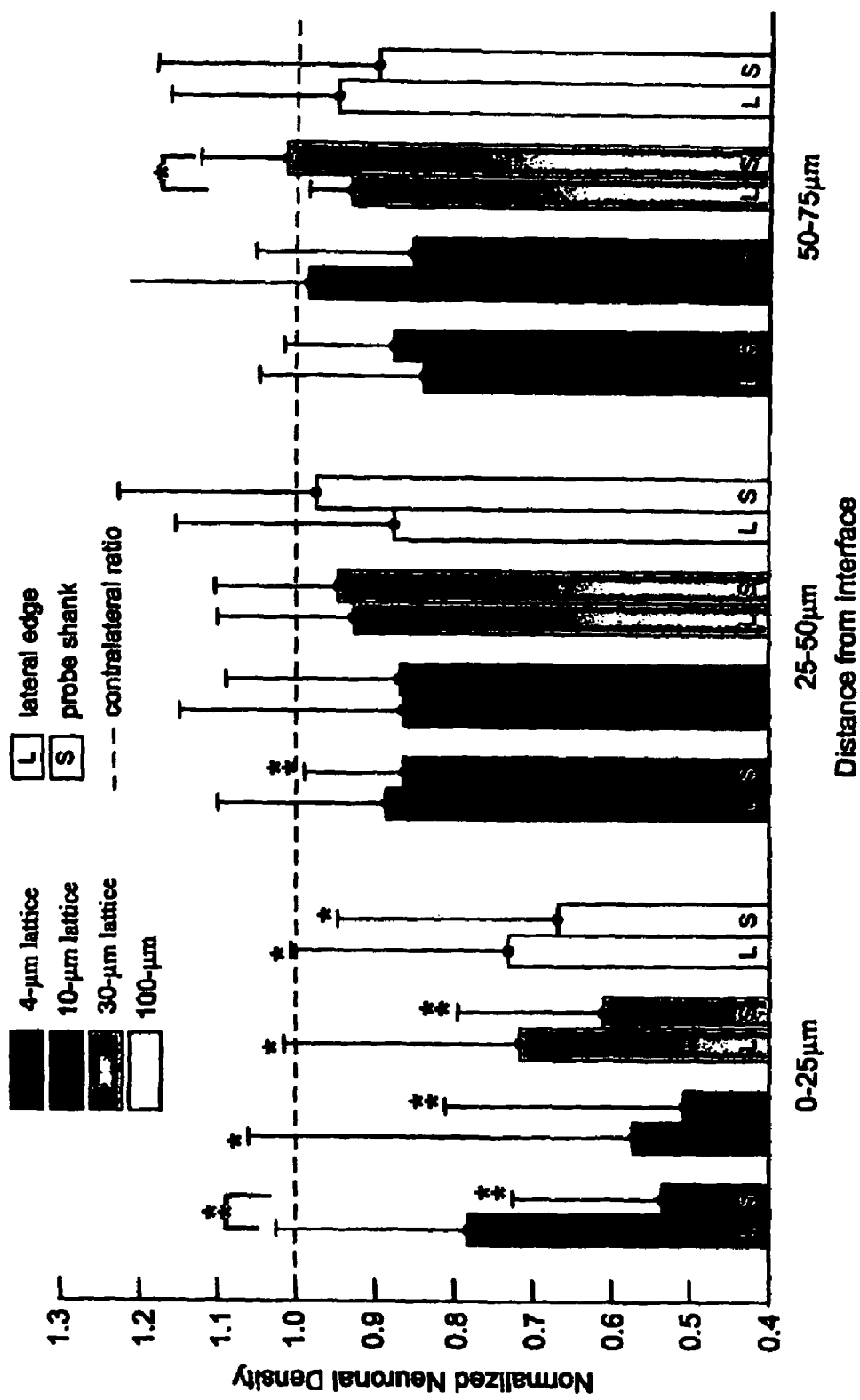
FIG. 11 shows normalized neuronal density around different probe types as a function of distance.
Figure 12:
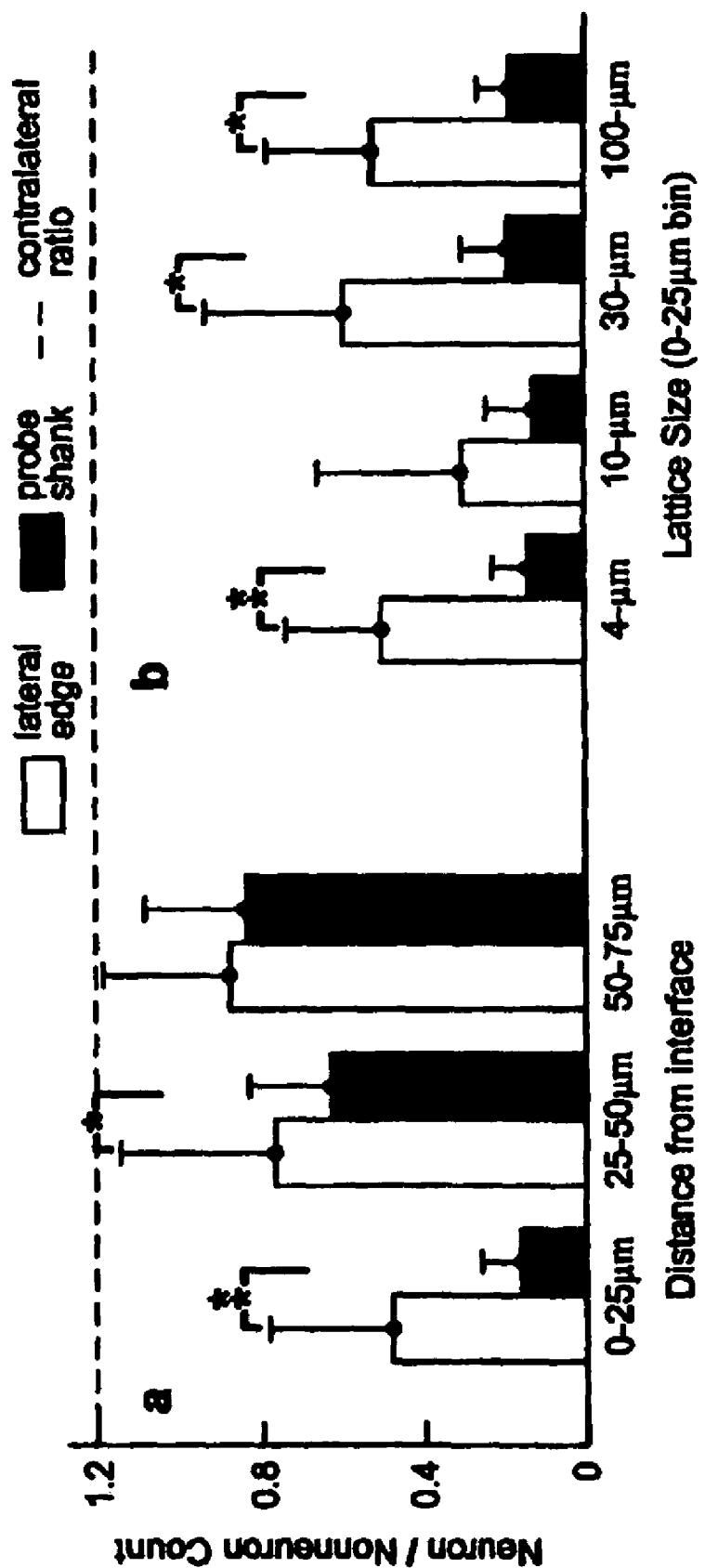
FIG. 12 is a summary of responses by neuron/nonneuron counts (N/NN ratio).

Cellular encapsulation was hypothesized to be dependent on the size of a given structure and the relative location of this structure on the device. In this context, we discuss the cellular density as a function of both lattice size (4, 10, 30-μm lattice structures, and 100-μm solid structure, all 5-μm thick) and the lateral edge (L) versus the probe shank (S). In FIGS. 10, 11, and 12, the response around the lateral edge and shank are paired together. Each region and distance bin in FIGS. 10 and 11 were normalized as described above. FIG. 10 shows IHC images showing NeuN+ reactivity (green) and Hoechst counterstain (blue) for each probe type. Probe type from left to right: 4 μm, 10 μm, 30 μm, 100 μm. Parylene auto-fluorescence has greatest intensity in violet spectrum where the lateral edge (L) and shank (S) are easily identifiable. Scale=100 µm. 40×Obj. FIG. 11 shows normalized neuronal density around each probe type as a function of distance. Density at the lateral edge (solid) and probe shank (hashed) are shown paired. All probes have significant neuronal loss in the 25-µm bin except the 4-µm lateral edge. Only the 4-µm lateral edge has a significantly greater density relative to the probe shank. Error bars denote S.D. (N=7 animals, *=p<0.05, **=p<0.02). FIG. 12 shows a summary of responses by neuron/nonneuron counts (N/NN ratio): FIG. 12(a)—mean ratio for all probes by distance bin N=28); FIG. 12 (b)—N/NN ratio for each lattice size (0-25 µm bin only, N=7). The contralateral hemisphere control value is 1.2 (dashed line). Error bars denote S.D. (*=p<0.05, **=p<0.005).

Cell Density in the Contralateral Hemisphere

Counting in the contralateral hemisphere of neuronal and nonneuronal cells defined the baseline for changes around the device-tissue interface. No significant differences between the lateral edge and probe shank control regions were present N=7 animals). The neuron-to-nonneuron (NIB ratio was 1.20, again with no significant difference between regions (data not shown). This indicated that 55% of all nuclei profiled in a 12-µm section were neurons (note that neuronal nuclei were considerably larger than Hoechst labeled nuclei and thus more were counted in a thin section).

Cellular Encapsulation

Figure 9:
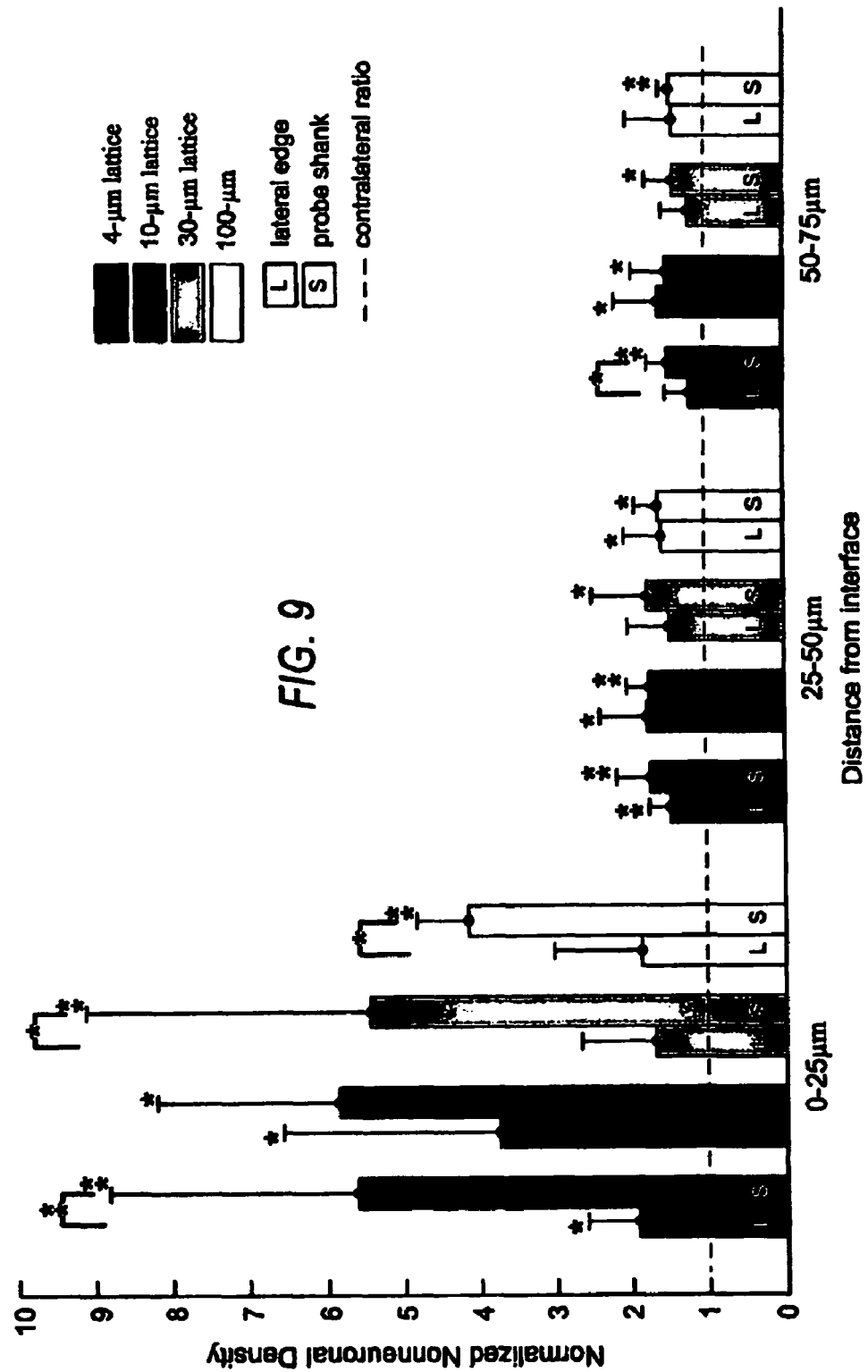
FIG. 9 shows nonneuronal density around different probe types as a function of distance.

The most significant improvement in cellular response was found between the shank and lateral structure within the first 25 µm for all probe geometries. FIG. 9 provides four representative confocal images for each probe type. NeuN immunolabeling (green) identified neurons and Hoechst counterstain (blue) identified nonneuronal cells. FIG. 9 shows nonneuronal density around each probe type as a function of distance. Density at the lateral edge (solid) and probe shank (hashed) are shown paired. 4, 30, and 100-µm probes have significance between the lateral edge and shank in the 0-25 µm bin. Error bars denote standard deviation (S.D.). (N=7 animals, *=p<0.05, **=p<0.02). Cell densities for each of the different lattice widths were not statistically different, either around the shank or lateral edge. However, there were more neurons and fewer nonneuronal cells around the lateral edge compared to the shank regardless of lattice width. When all probe types in the 0-25 µm bin from the interface were grouped (N=28 devices), the nonneuronal density was 2.29±1.76 around the lateral edge compared to 5.25±2.66 (p<0.000001) around the shank. This corresponds to a 329% relative reduction of encapsulation at the lateral edge.

Nonneuronal density for each probe geometry and distance bin was compared (FIG. 10). Overall, nonneuronal density was greatly above the control value in the 0-25 µm bin around the shank of each device. The 4 probe types were not statistically different, but comparison between the shank and the 5-µm thick lateral edge was significant. Significance between these two regions was greatest on the 4-µm probe (p<0.013). Neither the 30-µm or 100-µm lateral edge was significantly greater than the control values (contralateral tissue), but these also had larger standard deviations.

Encapsulation decreased dramatically around the shank in the 25-50-µm bin. In the 50-75-µm bin, the lateral edges of the 4, 30, 100-µm probes were not different than controls (values of 1.19, 1.21, and 1.41, respectively). Conversely, normalized nonneuronal cell density values around the shank of the devices ranged from 1.40 to 1.50, or a 40-50% increase.

Neuronal Density

The normalized neuronal density (FIG. 11) was also significantly different between the shank and the lateral edge regions. Neuronal loss was greatest in the first distance bin where the immediate injury and secondary injury were expected to be foremost. Neuronal loss was significant everywhere within 25 µm, except at the 4-µm lateral edge where the loss was just 22% compared to the controls. The neuronal density at the 4-µm edge was also significantly greater than at the shank region. However, it was not significantly larger than the density around the lateral region of wider lattice structures.

Testing for significance between each lattice size, whether comparing the lateral edge or the probe shank, did not reveal a difference (N=7). Again, the prevalent pattern was the contrast between the lateral edge and shank regions. When the normalized density was averaged for all probe types (N=28), the lateral edge value was 0.70±0.33 and the probe shank was 0.58±0.24 over the first 25 µm. This corresponds to a reduction in neuronal loss of 140% around the 5-µm thick edge relative to a 48-µm thick shank (p<0.03).

Neuron to Nonneuron Ratio

The neuron to nonneuron ratio (N/NN) was calculated to summarize the combined response of neuronal loss and nonneuronal gain—either of which could reduce the effectiveness of an electrophysiological sensor.

N/NN ratios averaged for all probe geometries and animals are plotted versus distance (FIG. 12(a)). In 26 out of 28 implants the N/NN mean was greatest at the lateral edge and averaged more than a 3× improvement (0-25-µm bin, N=28 implants, p<0.0000005). Significant improvement continued out to 50 µm (p<0.02). Further away from the interface, the benefit of the fine lateral edge was no longer notable. The N/NN ratio was still significantly lower than the control value of 1.2 (p<0.000005) for both the shank and lateral region.

In FIG. 12(b), the neuron-nonneuron ratio was averaged for each lattice size in just the 0-25 µm bin. The largest N/NN ratio was 0.60 at the lateral edge of a 30-µm probe. The greatest improvement was found between the 4-µm edge and the probe shank (360% difference, p<0.003). Again, probe types were not significantly different indicating that lattice width was not strongly influencing tissue reactivity in the region lateral to a probe.

Qualitative Results: Double Label Immunostaining

Several double labels were used to investigate the complex foreign body response around the device. Table 2 lists the number of animals and minimum number of sections for each combination. GFAP (astrocytes), OX-42 (microglia), NeuN (neurons), laminin, fibronectin, and neurofilament immunostain combinations improve our understanding of the cellular and extracellular protein interactions in the central nervous system (CNS).

To illustrate variations between the responses at the lateral edge region and the shank, we provide two columns of images selected based on the degree of reactivity (FIGS. 13-17) (all Scales=100 µm. 60×Obj.)

Figure 13:
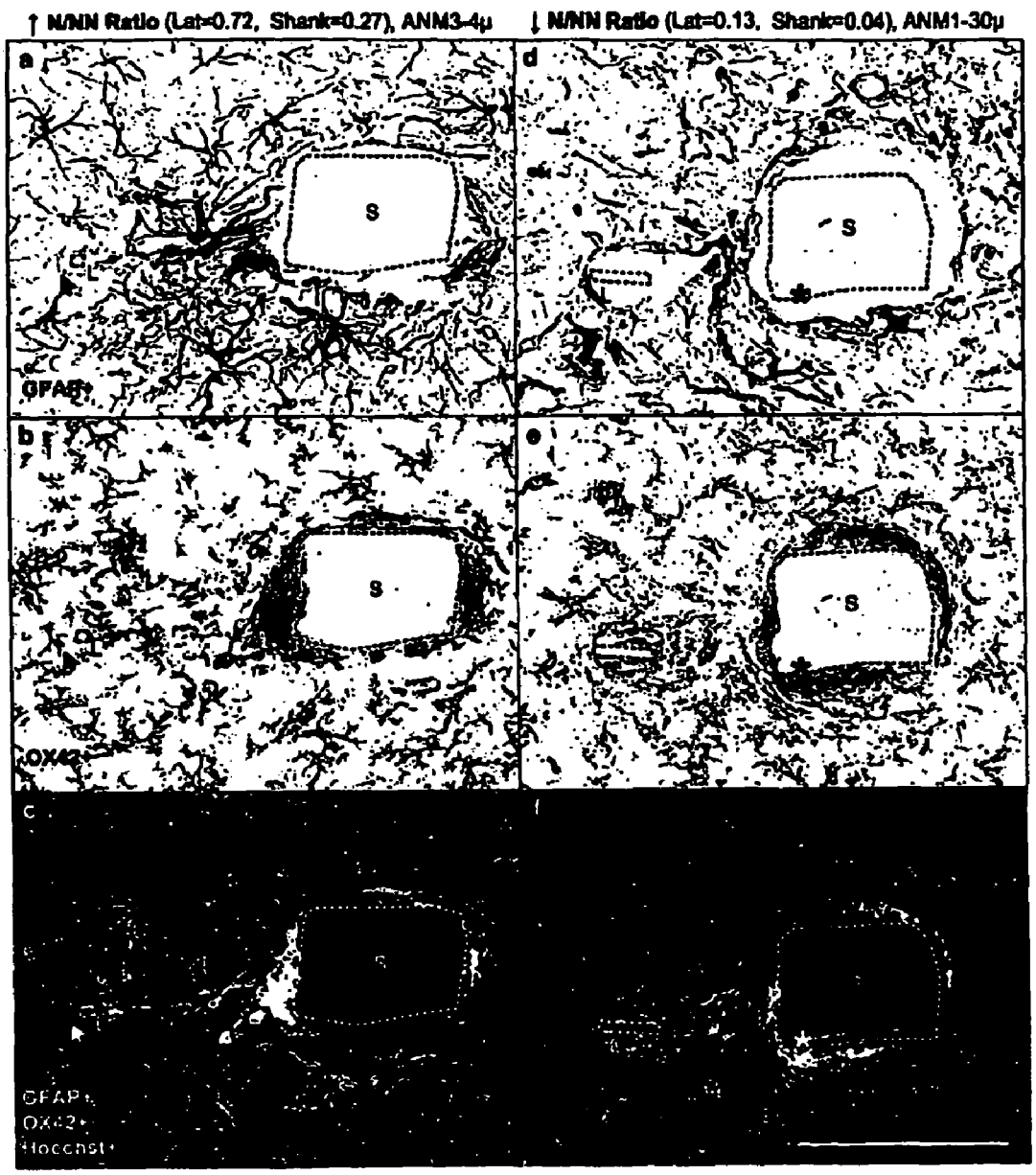
FIG. 13 is an inverted grayscale IHC images (a-b, d-c) showing GFAP+ (a,d) and OX-42+ reactivity (b,e) and the corresponding RGB color image including Hoechst+ (blue) (c,f).

FIG. 13 shows inverted grayscale IHC images (a-b, d-e) showing GFAP+ (a,d) and OX-42+ reactivity (b,e), and the corresponding RGB color image including Hoechst+ (blue) (c,f). Mean value of N/NN reported (N=8 sections). (a-c) An example of a high N/NN ratio. Reactivity around this type of interface was characterized by mild OX-42 reactivity, nearby ramified microglia, and OX-42+ concomitant with GFAP+ tissue (e.g. arrow). (d-f) Low N/NN interface was characterized by intense OX-42+ and a demarcation of GFAP reactivity (* in d-f). (Scale 100 µm. 60×Obj.)

Figure 14:
FIG. 14 is an inverted grayscale IHC images (a-b, d-e) showing GFAP+ (a,d) and NeuN+ reactivity (b,e), and the colocalization of these including Hoechst counterstain (blue) in RGB color (c,f).

FIG. 14 shows inverted grayscale IHC images (a-b,d-e) showing GFAP+ (a,d) and NeuN+ reactivity (b,e), and the colocalization of these including Hoechst counterstain (blue) in RGB color (c,f). (a-c) A high N/NN ratio was characterized by a concurrence of NeuN+ and GFAP+ (* in a,b) (d-f) Few neurons were near the low N/NN interface. In these cases, GFAP− and dense Hoechst+ tissue characterized the device interface and open-architecture region (arrows, d, f).

Figure 15:
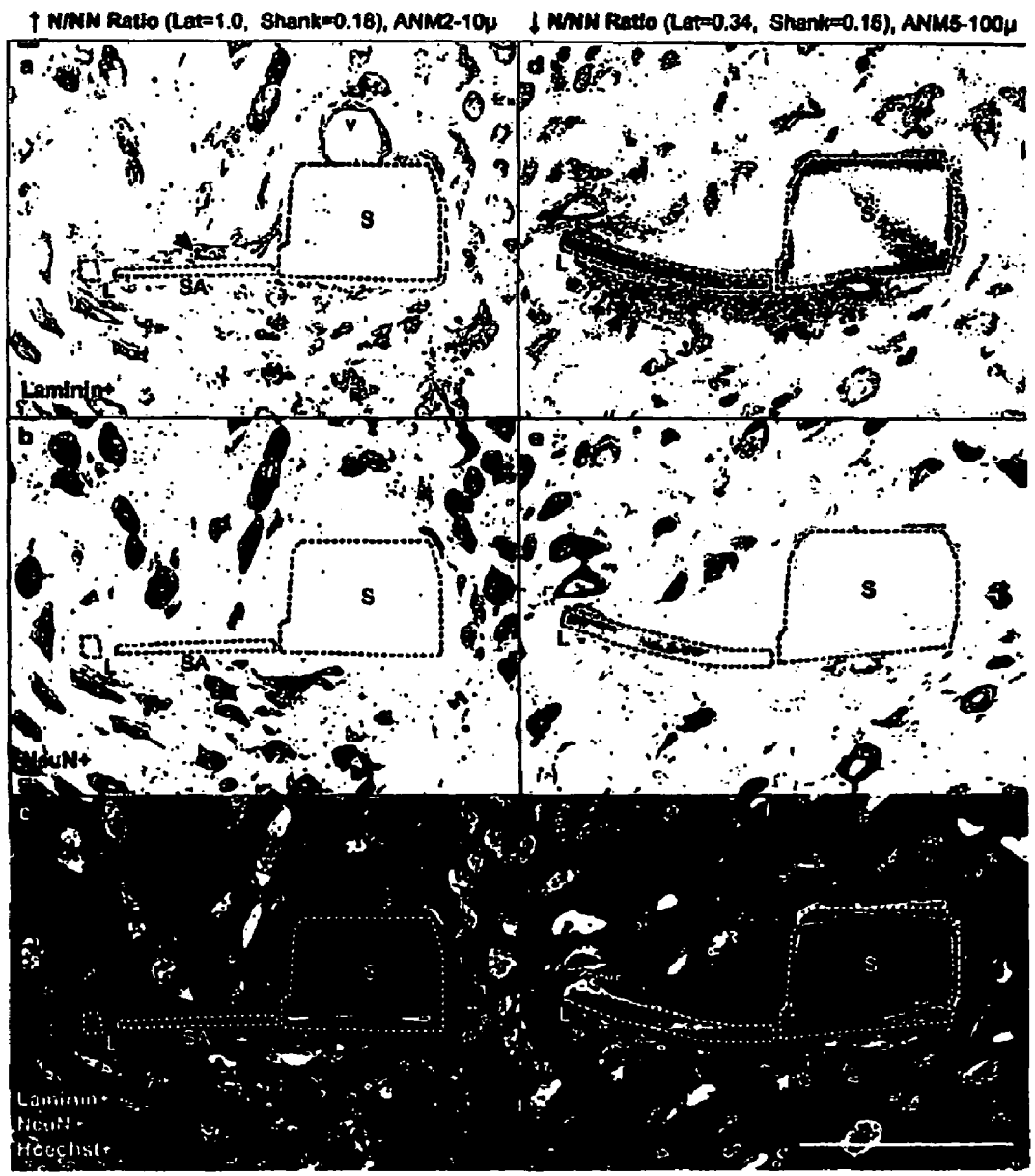
FIG. 15 is an inverted grayscale IHC images (a-b, d-e) showing laminin+ (a,d) and NeuN+ reactivity (b,e), and the corresponding RGB color image including Hoechst+ (blue) (c,f).

FIG. 15 shows inverted grayscale IHC images (a-b,d-e) showing laminin+ (a,d) and NeuN+ reactivity (b,e), and the corresponding RGB color image including Hoechst+ (blue) (c,f). (a-c) A high N/NN ratio was characterized by faint or non-existent laminin+ staining. Laminin intensity was only mild, even in the presence of a support arm (SA) (arrow in a,c). (d-f) A low N/NN response typically had a wide band of laminin deposition at the device interface but not at the lateral edge. Most characteristic of intense laminin staining was the presence of densely packed nuclei (arrows in d,f).

Figure 16:
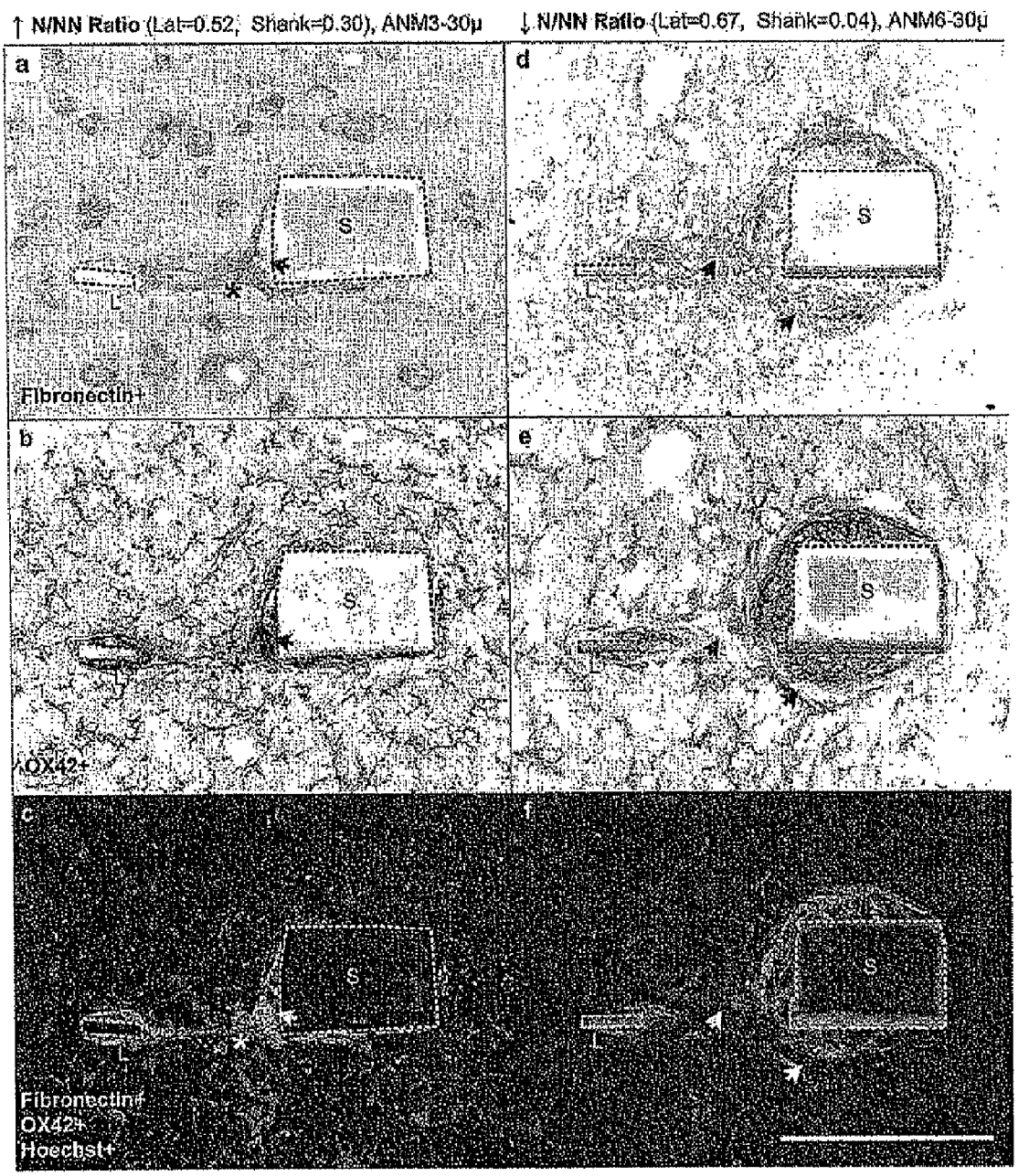
FIG. 16 is an inverted grayscale IHC images (a-b, d-e) showing fibronectin+ (a,d) and OX-42+ reactivity (b,e), and the corresponding RGB color image including Hoechst+ (blue) (c,f).

FIG. 16 shows inverted grayscale IHC images (a-b,d-e) showing fibronectin+ (a,d) and OX-42+ reactivity (b,e), and the corresponding RGB color image including Hoechst+ (blue) (c,f). Fibronectin staining had a pattern similar to laminin (a-c) The high N/NN-ratio had only a thin band of intensely labeled cells surrounded by ramified microglia just several microns distant. The inside corner of shanks (all probe types) usually exhibited intense OX-42 staining (b,e). (d-f) Fibronectin deposition extended 5 to 15 µm from the interface and was located with densely packed nonneuronal nuclei. While OX-42+ and fibronectin+ tissue were often concordant (* in a-c), highly encapsulated interfaces have non-overlapping regions suggesting that not all cells were microglia (arrows, a-f).

Figure 17:
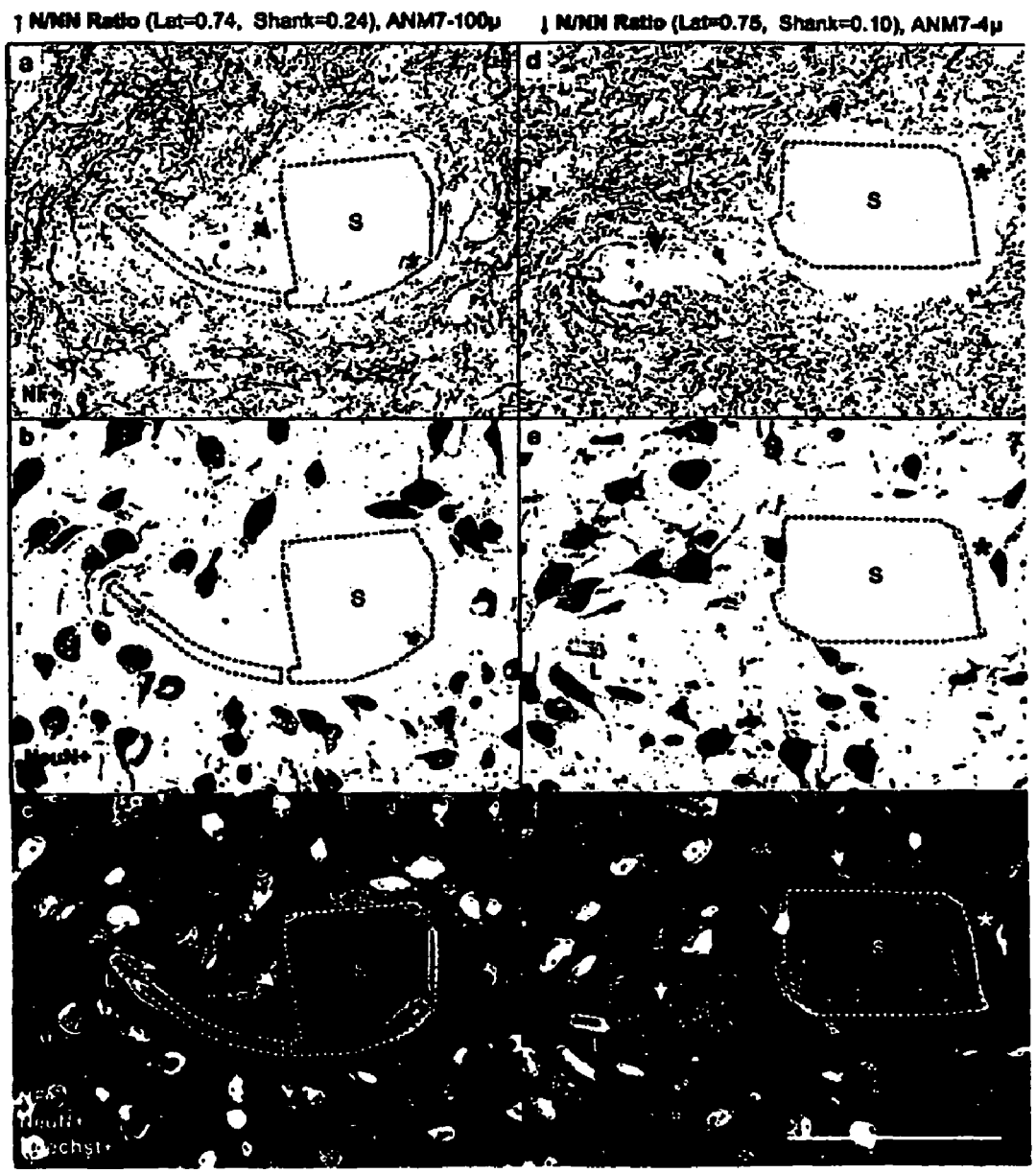
FIG. 17 is an inverted grayscale IHC images (a-b, d-c) showing neurofilament+ or NF+ (a,d) and NeuN+ reactivity (b,e), and the corresponding RGB color image including Hoechst+ (blue) (c,f).

FIG. 17 shows inverted grayscale IHC images (a-b,d-e) showing neurofilament+ or NF+ (a,d) and NeuN+ reactivity (b,e), and the corresponding RGB color image including Hoechst+ (blue) (c,f). NF+ tissue was generally in closer proximity to the device interface than neuronal nuclei. NF+ staining formed a band around dense nonneuronal nuclei (arrows a-f). Elongated neuronal nuclei were common when nuclei were adjacent to the structure (* in d-f).

At the top of each column, the mean value of the neuron to nonneuron ratio is provided. The histological responses and descriptions are representative of two extreme cases in the dataset. Note that the contrast in reactivity between the columns of images is not intended to compare lattice width. The greatest variation in N/NN values occurred around the probe shank and not the lateral edge, where there were few examples of low N/NN ratios.

GFAP and OX-42

Two key cellular types in any CNS injury are astrocytes and microglia. GFAP+ tissue indicates astrocyte structure, and as seen in FIG. 13, a stellate, intertwined morphology forms around the device-tissue interface. In the high N/NN example on the left, GFAP reactivity was evident within several microns of both the lateral structure and shank, although less intense in the former. Around the low N/NN example (FIG. 13(d-f), GFAP+ tissue circumscribed the implant shank and was approximately 10 µm distant from the shank. This demarcation between GFAP+ and densely packed nuclei (see FIG. 13(f)) was common wherever dense nuclei existed.

The OX-42 antigen is a CD11b integrin found on the surface of microglia and macrophages. Activated microglia exhibit an upregulation of CD11b and an ameboid shape with few processes. Microglia exhibit finely branched structures with little cytoplasm when unactivated [41]. This study shows OX-42 reactivity was greatest at the interface, and the intensity and thickness of OX-42+ tissue corresponded well with dense capsular nuclei, consistent with previous studies [10, 11, 14]. OX-42+ tissue around a high N/NN interface was characterized by a mildly intense, thin layer, and concomitant with GFAP+ tissue (arrow in FIG. 13). When the cellular encapsulation layer was dense, the intense OX-42+ region that dominates the interface was devoid of GFAP+ reactivity (* in FIG. 13).

The morphology of OX-42+ structures at the lateral edge (FIG. 13, 165) is important to note. Compact, ameboid structures were rarely observed at the outside lateral edge; instead, finely branched processes were evident. While microglia were present around the lateral structure, qualitatively these cells did not exhibit the same morphology and compactness as those around the probe shank.

In summary, the regions around the far lateral edge had less encapsulation and OX-42 reactivity relative to the shank. The morphology of OX-42+ structures also indicated a difference in phenotype between regions, GFAP+ tissue was always present at the lateral edge, but not always present immediately around the shank interface.

GFAP and NeuN

GFAP was present at the interface when cellular encapsulation was sparse (FIG. 14(a,e)) and displaced when the capsular cells were dense (FIG. 14(b,f)). Only occasionally was GFAP+ tissue observed deeply penetrating pockets of dense nuclei. NeuN+ structures were commonly found in and around intense GFAP+ tissue. Hypertrophied astrocyte-like processes were noted to extend around NeuN+ tissue when neurons were near the implant surface. This colocation of astrocytes and neurons was expected [15]. In the two examples shown, neurons can be seen adjacent to the central lattice region and enveloped by GFAP+ filaments (* in FIG. 14). Incidences of neuronal survival within several microns of the lattice region occurred in only three subjects.

Laminin and NeuN

Laminin is an extracellular matrix protein found in basal lamina and scar tissue. Laminin+ tissue in the brain normally consists of the basal lamina around vasculature and the meninges, and has been reported to be deposited by meningeal cells after a stab wound injury [15, 42]. Examples of a high and low N/NN value are shown in FIG. 15. The left column includes the support arm of a lattice structure, but despite this there was only a mildly intense band of laminin around the arm (see arrow), less around the shank, and none at the lateral edge. In the right column, a thick band was at the face of the 100-µm device, as was a conglomeration of nonneuronal nuclei. Laminin+ tissue was rarely visible at the outside lateral edge.

Fibronectin and OX-42

Fibronectin labels meningeal fibroblasts in the CNS [12, 43] and, like laminin, is a constituent of basal lamina. Fibronectin immunolabeling revealed a similar pattern of reactivity as observed with laminin. In high N/NN examples (FIG. 16 (a-c), fibronectin and OX-42 reactivity was limited to the immediate device interface and the inside corner of the probe (* in FIG. 16(a-c)). The low N/NN example (FIG. 16(d-f)) has a wider tract around the device, except at the lattice edge. OX-42+ tissue followed a similar profile, but was more prevalent than fibronectin+ tissue. Interestingly, in many cases where encapsulation was pronounced, OX-42+ and fibronectin+ were similar in pattern but not always overlapping (arrows in FIG. 16). In many other images (data not shown), fibronectin and laminin was not present. In general, OX-42+ reactivity was common at all probe interfaces and geometries. The intensity and thickness of OX-42+ tissue was consistently greater around the shank relative to the lateral edge.

Neurofilament and NeuN

The neurofilament antibody (NF+) used in this study labels medium sized intermediate filaments found in neurons only. Neurofilaments are found in axons and dendrites, which are necessarily severed during device insertion. NF+ tissue was within several microns of the high N/NN example and immediately adjacent to the lateral edge (FIG. 17(*a-c*)). NeuN proximity and density also indicated a favorable neural interface, again, particularly at the lateral edge. In tissue with greater reactivity (FIG. 17(*d-f*), NF-tissue formed a wider band around the shank. The tissue at the lateral edge was NF+ and NeuN+.

In general, neurofilament forms a pattern around the probe that closely matched that of GFAP+ reactivity with the exception that GFAP was confluent inside the lattice regions whereas NF+ was not. Like GFAP, NF staining was not present where nonneuronal cells were dense.

Reactivity in the Lattice Region

As can be seen in FIGS. 13-17, the reactivity in the inside corner (nearest the shank) is often intense, and sometimes even greater than around the shank. In the middle of the lattice region we see a variety of responses—from highly OX-42 and fibronectin reactive to the other extreme of GFAP and NeuN reactive. The presence of neurons was only occasionally seen and not necessarily "inside" the implant lattice. In general, the encapsulation and OX-42 reactivity of the lattice region was similar to that found around the shank of the device, and with no apparent dependence on lattice size (data not quantified).

Figure 18:
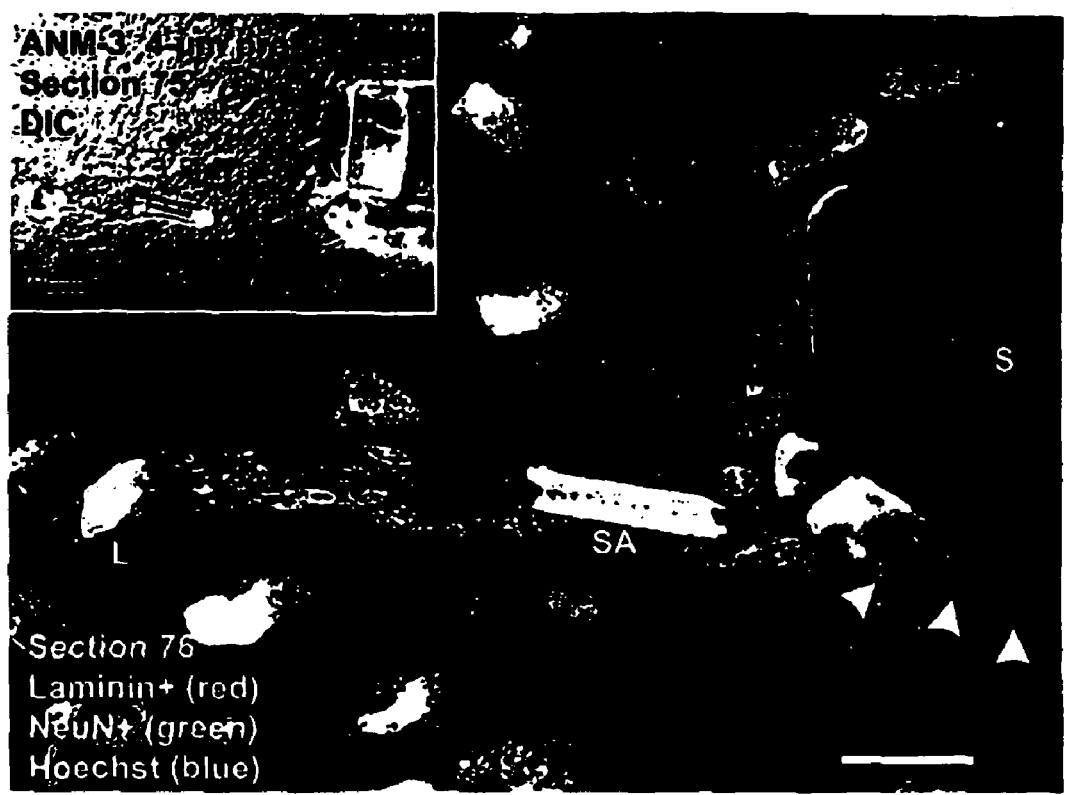
FIG. 18 illustrates reactivity around a support arm of a 4-µm lattice structure.

An example confocal image showing a support arm segment succinctly captures a pattern found around the three regions of interest—probe shank, lattice region, and lateral edge (FIG. 18). The first layer of parylene around the shank has been rotated 90° due to cryosectioning or processing and effectively provides a coronal view of nuclei adhering to its surface (see arrows). The nuclei were disc-shaped and relatively large. Around the support arm, three-dimension confocal images (not shown) revealed the nuclei to be elongated in one dimension—along the length of the support arm. The morphology of nuclei at the outside lateral edge were relatively small, spherical, and sparsely packed. These nuclei were rarely elongated or conformal to the edge despite this structure having identical dimensions as the support arm. Additionally, intense but narrow laminin+ tissue was outlining the shank and support arm structures, but not the outside edge.

Discussion

The contrast in encapsulation and neuronal loss between the shank and lattice edge described above demonstrates a differential chronic tissue response, which correlates to the overall geometry and structural dimensions of the device. The degree of neuronal loss reported here is smaller than two other quantitative reports on the biocompatibility of neural probes [11, 16]. Edell et al. reported significant loss (90% confidence level) in two rabbits out to 10 and 60 μm from the interface of silicon shanks (40 by 60-μm cross-section). Using a slightly different metric, Biran et al. (2005) reported a loss of 40% around a silicon probe in a 100-μm radius from the interface at both 2 and 4 weeks (15-μm by ~150-μm cross-section). When we averaged across all probes (N=28) for a 75-μm radius, the shank region had a loss of 17%, and in the lateral region the loss was only 12% (calculated from FIG. 11 and weighted by area). Significant loss did not extend beyond the first 25 μm for any probe type (N=7). This study used a stereotaxic frame for insertion, intraparenchymal probes, and a different substrate material—any of which may account for the differences between studies. Nonetheless, we are encouraged by the comparatively healthy interface around the shank of parylene probes, and that despite this we found significant advantage at the lateral edge. A direct comparison of encapsulation density is not possible since prior studies have not quantified this effect, but the variability and extent of encapsulation seems comparable [10, 11, 26, 44]

Although there is some information that the microscale geometry of a biomaterial may modulate cellular responses, we are not aware of any that correlate microelectrode geometry with reduced tissue encapsulation, as we have discovered. One in vitro study reported that macrophages do not adhere to or spread on polymer fibers ranging in diameter from 2 to 12 μm [33]. An in vivo study investigated the effect of polymer fiber diameters from 2-27 μm of single fiber strands in the rat subcutis [34]. The results showed a marked decrease in capsular thickness around fiber diameters in the 2.1 to 5.9-μm group. Cellular spreading can turn on or off apoptosis or growth and this conformation can be regulated by adhesive substrate patterns [35-37].

We have investigated substrate geometry, feature size, and cellular mechanotransduction in the context of microelectrode design to evaluate whether there was be a differential decrease in encapsulation around a thin) lateral structure over a conventional penetrating shank because the lateral structure has a sub-cellular "footprint" and extends far from the shank where tissue damage and encapsulation density is expected to be greatest. Furthermore, we evaluated whether, if the surface area of the thin, lateral structure were reduced by creating a lattice-like geometry, tissue encapsulation is further mitigated relative to larger lattice sizes or no lattice whatsoever.

Our results support our first hypothesis: when sufficiently distant from the shank, the far lateral region on a 5-μm thick structure would have less encapsulation and neuronal loss. One explanation of these results is a biomimetic principle positing that cells are less reactive to dimensions found naturally in the brain. More specifically, below a certain dimension the cell may not be able to attach, spread, and create tension in the cytoskeleton, which in turn disrupts the mechanotransduction pathway that normally induces the unfavorable response [34, 36, 37, 45]. While other studies have previously investigated cross-sectional area aid found no long-term advantages [10], this study examined structural dimensions on the subcellular scale (all lateral edges are 5-μm thick). Again, this can be explained by a dimensional threshold effect [34]. In addition to the quantitative evidence, we believe the altered morphology seen around the various probe structures (FIG. 18) supports this theory. FIG. 18 exemplifies the reactivity around the support arm of a 4-μm lattice structure. Two consecutive sections are shown, a DIC and IHC color image. Given a slight offset in the transverse sectioning angle, only a portion of the support arm (SA) was embedded in each. The tight but intense laminin staining in section 76 formed an outline of the support arm. Contrastingly, a single nucleus at the outside lateral edge was more spherical in shape. Cells on the surface of the implant shank conformed to the flat surface in a disc-like pattern (arrows). Shapes were evaluated using three-dimensional confocal images (not shown). Scale=20 μm. Along the shank the nuclei were disc-like and spread out on the face of the device. At the lateral edge, there were rarely nuclei immediately present and nearby nuclei had smaller, spherical forms.

A more speculative theory is related to the degree of tissue damage and compression upon insertion. Consider that the tested shank cross-sectional area is nearly 7 times greater than the 5 by 100-μm area of the lateral structure (FIG. 5(*e'*)). Furthermore, the displaced volume per unit length (cross-sectional length) is even smaller around the lateral structure, which may be a useful concept when considering the concentration and diffusion of fluids immediately around the interface. After insertion, the region around the probe shank may have a higher concentration of neurotoxic substance since the damage and compression is focused here with less surrounding tissue volume. This initial concentration may in turn be proportional to the neuronal loss and degree of encapsulation at the 4-week time point. In short, we believe the foreign body response to the subcellular edge dimension is likely the most important phenomenon contributing to the favorable response; however, we cannot rule out a contribution related to the nature of the acute injury as well.

Our second hypothesis was that the smallest lattice size (4 by 5 µm) would induce the least tissue reactivity. Testing for significance between lattice sizes, whether comparing across lattice structures or the probe shank, did not indicate one lattice edge had any less encapsulation or neuronal loss over another. While the second hypothesis does not firmly obtain in our current analysis, there were several possible confounding factors. Most importantly, an open-architecture lattice structure presents a very different mechanical interface than a solid structure (i.e., shank). The brain is continually pulsating due to vascular and respiratory oscillations, and so small relative movement (micromotion) between an implant and tissue induces some level of strain [46-48]. Recently it was reported that the pial surface in the rat oscillates by as much as 30 µm during normal respiration [48]. This suggests that compressive forces and not just shear forces are at play within the lattice regions. Also, stress may be localized at edges and inside corners. The support arms and lateral structure were identical, but a consistent difference in reactivity was evident (FIGS. 13-18), so more than size was influencing local reactivity. Additional confounding factors that are difficult to control for include surface area and "open-architecture" area.

Despite considerable tissue reactivity inside the lattice region, several advantages may exist for an open-architecture design. The lattice design may (1) provide improved tissue integration and (2) re-establish communication between either neurons or astrocytes that were initially severed during insertion. Liu and McCreery (1999, 2006) reported that neuronal stability increases with time post-implant and is believed to the result of tissue encapsulation anchoring the probes in place [23, 49]. It is reasonable to suggest that a lattice design will quicken the stabilization process (which is typically 2-3 months), which is an important factor in brain-machine applications. Normal forces inside the lattice structure should reduce probe migration. Re-establishing more neuronal and astrocytic (Ca2+ gap junctions) communication after injury both around and through the probe may be important for maintaining functional neurons. The lattice design would, in theory, enable more cell-cell contact.

The double label immunostaining revealed two different types of glial scar. The first and more benevolent was a thin boundary of activated microglia at the interface intermingled with hypertrophied astrocytic processes. Unlike activated microglia, the hypertrophied astrocytes usually coexisted with neurons (neurofilament+ and NeuN+ tissue). This type characterized the tissue about the lateral edge and only occasionally the region about the shank. The second type of reactive tissue was a noticeably thicker capsular region devoid of GFAP, neurofilament, and NeuN but always OX-42 positive and often fibronectin and laminin positive as well. Here the neuronal loss and nonneuronal encapsulation is most evident. However, the variability at the lateral edge of these probes was far less. The tissue in this region was consistently laminin negative, fibronectin negative, and GFAP positive. Further, microglia and other nonneuronal cells did not conform to the edge of the structure and thus may contribute less to the electrical impedance between this point on the device and a distant neuron.

One theory that could explain the two types of glial scar around the shank of the device is the presence or lack of meningeal cells. Meningeal cells have been reported to play an active role in stab wound injuries and form an "accessory glia limitans" [12, 15, 42, 43]. Some have suggested their presence around neural implants [13, 29]. The presence of fibronectin+/OX-42—tissue suggests that some of the non-neuronal nuclei (Hoechst+) may be fibroblasts of meningeal origin. Their presence would explain why astrocytes seemingly circumscribe the tissue several to tens of microns from the shank, and why some tissue is fibronectin+ but not OX-42+. This is important because the existence of fibroblasts and the resulting astrocyte-meningial interface may farther increase the impedance between the electrode and spiking neurons [50].

Regarding the fabrication of the test structures, we chose a substrate of poly-para-xylylene (specifically parylene-C) for several reasons: (1) microfabrication techniques are well established, (2) Class VI USP biocompatibility rating, (3) excellent insulating properties [51], (4) low water uptake of 0.06%, (5) elongation at break is 200% [52], and (6) a polymer implant can be left in situ to improve the spatial resolution of the histological analysis. While the device surface was parylene, the core of the shank consisted of SU-8, an epoxy based photoresist that has been well characterized. This material can achieve thick layers in one application whereas parylene is typically deposited less than 10 µm each run. SU-8 is also reported to be biocompatible [53, 54]. However, other biocompatible materials such as silicon dioxide, silicon, and polyimide to name a few, would be expected to confer the same results if designed with similar dimensions.

The pattern of cellular encapsulation and neuronal loss suggests an electrode site design that wraps-around the perimeter. To effectively use the limited substrate at the perimeter around a biosensor in the CNS, the electrode surface should be on three sides of the device as shown in FIG. 18 (data taken from FIG. 11(*a*)). FIG. 18 is a graphical illustration of tissue encapsulation around a cross-section of the device representing the typical chronic tissue reactivity and encapsulation around a sample LEP. Improved long-term efficacy of the LEP over conventional multielectrode probes is derived from the significant reduction of cellular and acellular tissue encapsulation, either in terms of reduced density or reduced thickness.

Figure 19:
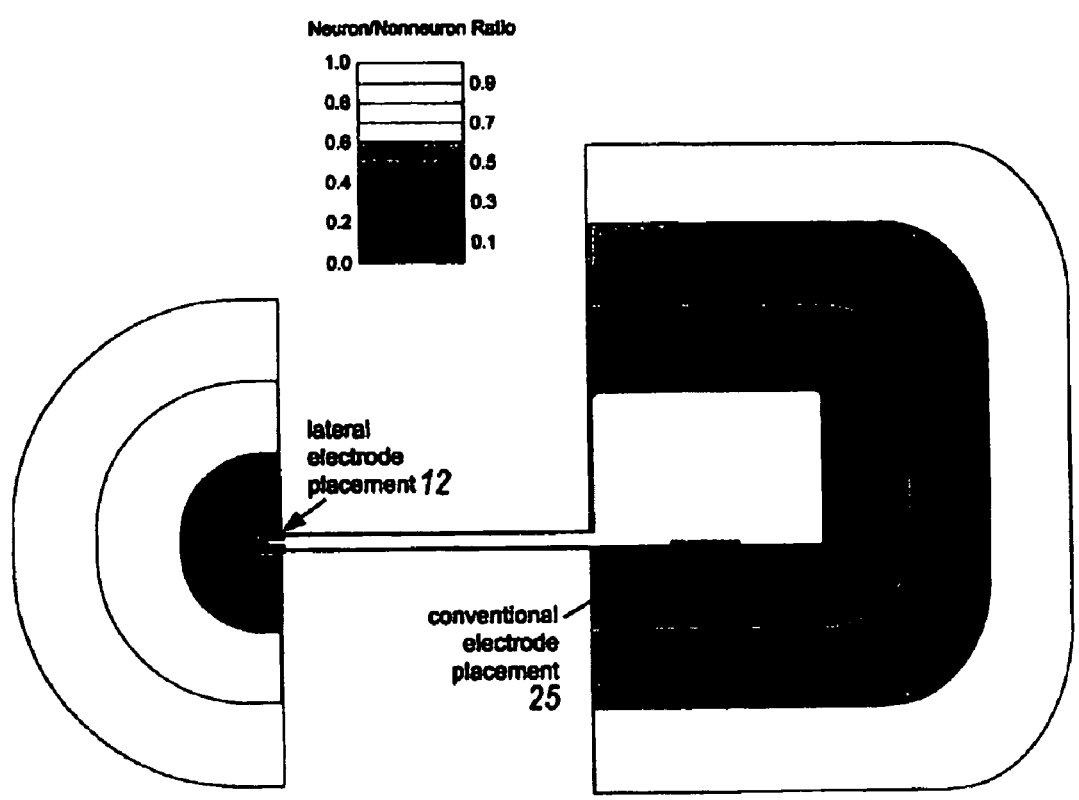
FIG. 19 is a graphic of tissue encapsulation around a cross-section of a device representing the average neuronal to nonneuronal cellular around the microelectrode structures tested in accordance with one embodiment.

The pattern of cellular encapsulation and neuronal loss suggests possible additional benefit of an electrode site design that wraps around the perimeter. To more effectively use the substrate at the perimeter around a biosensor implanted in the central nervous system, in some embodiments, a portion of electrode site surface may be disposed partially on or in three sides of the device as shown in FIG. 19 (data taken from FIG. 12 (*a*)). Another benefit of such a design would be an increase in the sensor contact radius from 180 degrees [55] to almost 360 degrees because there is less shielding. However, there are two possible difficulties herein: (1) the fabrication complexity of creating a three dimensional electrode site on a planar substrate, and (2) the size and surface limitation imposed may reduce sensitivity. In the case of a neural probe, we believe these are attainable engineering goals. Regarding the former concern, one may use electroplating to create a thick electrode, which is commonly done with contact vias in integrated and printed circuits. To address the latter, the effective surface area can be greatly increased with the use of platinum black [56], oxidized iridium [57], or conductive polymers [29]. In some applications, such as recording spike activity, sensitivity is expected to increase with decreased surface area [55].

CONCLUSIONS

Quantification of high resolution confocal images around intact probe structures revealed that encapsulating cell density within 25 μm of a thin lateral structure is reduced by more than 300% relative to the shank. The difference in neuronal loss was also significant, although less so. Furthermore, activated microglia and protein deposition are greatly reduced at this surface. Our study also verified that despite utilizing a polymer substrate and subcellular dimensions, these devices are mechanically robust and practical as neural implants.

Our study showed that, in some embodiments, without limitation, more ideal electrode site placement for the tested implants is on the outermost edge of about a 5-μm thick structure extending far from the device shank, which may be implanted into biological tissue where desired, as some examples only, in the central nervous system and elsewhere in vertebrates, including mammals (e.g., humans).

The preceding description has been presented only to illustrate and describe exemplary embodiments of the methods and systems of the present invention. It is not intended to be exhaustive or to limit the invention to any precise form disclosed. It will be understood by those skilled in the art that various changes may be made and equivalents may be substituted for elements thereof without departing from the scope of the invention. In addition, many modifications may be made to adapt a particular situation or material to the teachings of the invention without departing from the essential scope. Therefore, it is intended that the invention not be limited to the particular embodiment disclosed as the best mode contemplated for carrying out this invention, but that the invention will include all embodiments falling within the scope of the claims, including among them, any equivalents. The invention may be practiced otherwise than is specifically explained and illustrated without departing from its spirit or scope.

REFERENCES

1. Evarts E V. Pyramidal tract activity associated with a conditioned hand movement in the monkey. J Neurophysiol 1966; 29(6) 1011-27.
2. Schmidt E M. An instrument for separation of multiple-unit neuroelectric signals, IEEE Trans Biomed Eng 1971; 18(2):155-7.
3. Hochberg L R, Serniiya M D, Friebs G M, Mukand J A, Saleh M, Caplan A U, et al Neuronal ensemble control of prosthetic devices by a human with tetraplegia. Nature 2006; 442(7099): 164-71.
4. Schwartz A B. Cortical neural prosthetics. Amu Rev Neurosci 2004; 27:487-507.
5. Wisniewski N, Klitzman B, Miller B, Reichert W M. Decreased analyte transport through implanted membranes: differentiation of biofouling from tissue effects. J Biomed Mater Res 2001; 57(4):513-21.
6. Gilligan B C, Shualts M, Rhodes R K, Jacobs P G, Brauker J H, Pintar T J, et al. Feasibility of continuous long-term glucose monitoring from a subcutaneous glucose sensor in humans. Diabetes Technol Ther 2004; 6(3):378-86.
7. Ratner B D, Bryant S J. Biomaterials: where we have been and where we are going. Annu Rev Biomed Eng 2004; 6:41-75.
8. Stensaas S S, Stensaas L J. Histopathological evaluation of materials implanted in the cerebral cortex, Acta Neuropathol (Berl) 1978; 41(2):145-55.
9. Maynard E M, Feinandez E, Normann R A. A technique to prevent dural adhesions to chronically implanted microelectrode arrays. J Neurosci Methods 2000; 97(2):93-101.
10. Szarowski D H, Andersen M D, Retterer S, Spence A J, Isaacson M, Craighead H G, et al. Brain responses to micro-machined silicon devices. Brain Res 2003; 983(1-2):23-35.
11. Biran R, Martin D C, Tresco P A. Neuronal cell loss accompanies the brain tissue response to chronically implanted silicon microelectrode arrays. Exp Neurol 2005; 195(1):115-26.
12. Shearer M C, Fawcett J W. The astrocyte/meningeal cell interface—a barrier to successful nerve regeneration? Cell Tissue Res 2001; 305(2):267-73.
13. Kim Y T, Hitchcock R W, Bridge M J, Tresco P A, Chronic response of adult rat brain tissue to implants anchored to the skull. Biomaterials 2004; 25(12):2229-37.
14. Hampton D W, Rhodes K E, Zhao C, Franklin R J, Fawcett J W. The responses of oligodendrocyte precursor cells, astrocytes and microglia to a cortical stab injury, in the brain. Neuroscience 2004; 127(4):813-20.
15. Fawcett J W, Asher R A. The glial scar and central nervous system repair. Brain Res Bull 1999; 49(6):377-91.
16. Edell D J, Toi V V, McNeil V M, Clark L D, Factors influencing the biocompatibility of insertable silicon microshafts in cerebral cortex. IEEE Trans Biomed Eng 1992; 39(6):635-43.
17. Roitbak T, Sykmova B. Diffusion barriers evoked in the rat cortex by reactive astrogliosis Glia 1999; 28(1):40-8.
18. Sharkawy A A, Klitzman B, Traskey G A, Reichert W M. Engineering the tissue which encapsulates subcutaneous implants. II, Plasma-tissue exchange properties. J Biomed Mater Res 1998; 40(4):586-97.
19. Williams J C, Rennaker R L, Kipke D R. Long-term neural recording characteristics of wire microelectrode arrays implanted in cerebral cortex. Brain Res Brain Res Protoc 1999; 4(3):303-13.
20. Johnson M D, Otto K J, Kipke D R. Repeated voltage biasing improves unit recordings by reducing resistive tissue impedances. IEEE Trans Neural Syst Rehabil Eng 2005; 13(2):160-5.
21. Ludwig K A, Uram J D, Yang I, Martin D C, Kipke D R. Chronic neural recordings using silicon microelectrode arrays electrochemically deposited with a poly(3,4-ethylenedioxythiophene) (PEDOT) film. J Neural Eng 2006; 3(1):59-70.
22. Nicholson C, Sykova B. Extracellular space structure revealed by diffusion analysis. Trends Neurosci 1998; 21(5):207-15.
23. Liu X, McCreery D B, Carter R R, Bullara L A, Yuen T G, Agnew W F. Stability of the interface between neural tissue and chronically implanted intracortical microelectrodes. IEEE Transactions on Rehabilitation Engineering 1999; 7(3):315-26.
24. Schmidt E M, McIntosh J S, Bak M J. Long-term implants of Parylene-C coated microelectrodes. Med Biol Eng Comput 1988; 26(1):96-101.
25. McCreery D B, Agnew W F, McHardy J. Electrical characteristics of chronically implanted platinum-iridium electrodes. IEEE Transactions on Biomedical Engineering 1987; 34(9):664-8.
26. Rousehe P J, Normaun R A. Chronic recording capability of the Utah Intracortical Electrode Array in cat sensory cortex. Journal of Neuroscience Methods 1998; 82(1):1-15.

27. Lefurge T, Goodall E, Horch K, Stensaas L, Schoenberg A. Chronically implanted intrafascicular recording electrodes. Ann Biomed Eng 1991; 19(2):197-207.
28. He W, Bellamrkonda R V. Nanoscale neuro-integrative coatings for neural implants. Biomaterials 2005; 26(16): 2983-90.
29. Cui X, Lee V A, Raphael Y, Wiler J A, Hetke J F, Anderson D J, et al. Surface modification of neural recording electrodes with conducting polymer/biomolecule blends. J Biomed Mater Res 2001; 56(2):261-72.
30. Zhong Y, Bellamklonda R V. Controlled release of anti-inflammatory agent alpha-MSH from neural implants. J Control Release 2005; 1006(3):309-18.
31. Kim D H, Martin D C, Sustained release of dexamethasone from hydrophilic matrices using PLGA nanoparticles for neural drug delivery. Biomaterials 2006; 27(15):3031-7.
32. Shain W, Spataro L, Dilgen J, Haverstick K, Retterer S, Isaacson M, et al. Controlling cellular reactive responses around neural prosthetic devices using peripheral and local intervention strategies. IEEE Trans Neural Syst Rehabil Eng 2003; 11(2):186-8.
33. Bernatchez S F, Parks P J, Gibbons D F. Interaction of macrophages with fibrous materials in vitro, Biomaterials 1996; 17(21):2077-86.
34. Sanders J E, Stiles C E, Hayes C L. Tissue response to single-polymer fibers of varying diameters: evaluation of fibrous encapsulation and macrophage density. J Biomed Mater Res 2000; 52(1):231-7.
35. Turner A M, Dowell N, Turner S W, Kam L, Isaacson M, Turner J N, et al. Attachment of astroglial cells to microfabricated pillar arrays of different geometries. J Biomed Mater Res 2000; 51(3):430-41.
36. Chen C S, Tan J, Tien J. Mechanotransduction at cell-matrix and cell-cell contacts Annu Rev Biomed Eng 2004; 6:275-302,
37. Chen C S, Mrksich M, Huang S, Witesides G M, Ingber D E. Geometric control of cell life and death. Science 1997; 276(5317):1425-8.
38. Rousche P J, Normann R A. A method for pneumatically inserting an array of penetrating electrodes into cortical tissue. Ann Biomed Eng 1992; 20(4):413-22.
39. Vetter R J, Williams J C, Hetke J F, Nunamaker R A, Kipke D R. Chronic neural recording using silicon-substrate microelectrode arrays implanted in cerebral cortex, IEEE Trans Biomed Eng 2004; 51(6):896-904.
40. Bjornsson C S, Oh S J, Al-Kofahi Y A, Lim Y J, Smith K L, Turner J N, et al. Effects of insertion conditions on tissue strain and vascular damage during neuroprosthetic device insertion. J Neural Engineering 2006; 3(10):196-207.
41. Schwartz M, Butovsky O, Bruck W, Hanisch U K. Microglial phenotype: is the commitment reversible? Trends Neurosci 2006; 29(2):68-74.
42. Shearer M C, Niclou S P, Brown D, Asher R A, Holtmaat A J, Levine J M, et al. The astrocyte/meningeal cell interface is a barrier to neurite outgrowth which can be overcome by manipulation of inhibitory molecules or axonal signalling pathways. Mol Cell Neurosci 2003; 24(4):913-25.
43. Bundesen L Q, Scheel T A, Bregman B S, Kromer L F. Ephrin-B2 and EphB2 regulation of astrocyte-meningeal fibroblast interactions in response to spinal cord lesions in adult rats. J Neurosci 2003; 23(21):7789-800.
44. Turner J N, Shain W, Szarowski D H, Andersen M, Martins S, Isaacson M, et al. Cerebral astrocyte response to micromachined silicon implants. Exp Neurol 1999; 156 (1):33-49.
45. Brauker J H, Carr-Brendel V E, Martinson L A, Crudele J, Johnston W D, Johnson R C. Neovascularization of synthetic membranes directed by membrane microarchitecture, J Biomed Mater Res 1995; 29(12):1517-24.
46. Goldstein S R, Salcman M. Mechanical factors in the design of chronic recording intracortical microelectrodes. IEEE Trans Biomed Eng 1973; 20(4):260-9.
47. Subbaroyan J, Martin D C, Kipke D R. A finite-element model of the mechanical effects of implantable microelectrodes in the cerebral cortex. J Neural Eng 2005; 2(4): 103-13.
48. Gilletti A, Mushuswamy J. Brain micromotion around implants in the somatosensory corex of rats. J Neural Eng 2006; 3:189-195.
49. Liu X, McCreery D B, Bullara L A, Agnew W F. Evaluation of the stability of intracortical microelectrode arrays. IEEE Trans Neural Syst Rehabil Eng 2006; 14(1):91-100.
50. Merrill D R, Tresco P A. Impedance characterization of microarray recording electrodes in vitro. IEEE Trans Biomed Eng 2005; 52(11): 1960-5.
51. Loeb G E, Peck R A, Martyniuk J. Toward the ultimate metal microelectrode. J Neurosci Methods 1995; 63(1-2): 175-83.
52. Fortin J B, Lu T M. Chemical vapor deposition polymerization: the growth and properties of parylene thin films. Boston: Kluwer Academic Publishers; 2004.
53. Voskerician G, Shive M S, Shawgo R S, von Recum H, Anderson J M, Cima M S, et al. Biocompatibility and biofouling of MEMS drug delivery devices. Biomaterials 2003; 24(11):1959-67.
54. Kotzar G, Freas M, Abel P, Fleischman A, Roy S, Zorman C, et al. Evaluation of MEMS materials of construction for implantable medical devices. Biomaterials 2002; 23(13): 2737-50.
55. Moffitt M A, McIntyre C C. Model-based analysis of cortical recording with silicon microelectrodes. Clin Neurophysiol 2005; 116(9):2240-50.
56. Ilic B, Czaplewski D, Neuzil P, Stanczyk T, Blough S, Maclay G J. Preparation and characterization of platinum black electrodes. Journal of Materials Science 2000; 35(14):3447-57.
57, Lee I-S, Whang C-N, Choi K, Choo M-S, Lee Y-H. Characterization of iridium film as a stimulating neural electrode, Biomaterials 2002; 23(11):2375-80.

What is claimed is:

1. An implantable microelectrode comprising:
   a shank, and
   at least one electrode site,
   wherein the shank comprises a backbone portion and a laterally extending platform, the laterally extending platform having a thickness less than the backbone portion and extending up to about 250 microns radially from the backbone portion and
   wherein at least one electrode site is disposed at least partially on or in the laterally extending platform.

2. The implantable microelectrode of claim 1, wherein the laterally extending platform further comprises at least one longitudinal rib and at least one radially projecting rib projecting from the portion and wherein the configuration of the longitudinal rib, the radially extending rib, and the backbone portion form at least one open space in the laterally extending platform.

3. The implantable microelectrode of claim 2, wherein at least one electrode site is disposed at least partially on or in the longitudinal rib.

4. The implantable microelectrode of claim 1 or 2, wherein the laterally extending platform has a thickness between about 0.5 and 10 microns.

5. The implantable microelectrode of claim 1 or 2, wherein the at least one electrode site includes a plurality of microelectrodes disposed on the laterally extending platform.

6. The implantable microelectrode of claim 5, wherein at least one of the electrode sites is disposed on the most lateral edge of the laterally extending platform or within about 10 microns of the most lateral edge.

7. The implantable microelectrode of claim 1 or 2, wherein the shank further comprises a tip whose shape is chiseled, conical, frusto-conical, or any combination thereof.

8. The implantable microelectrode of claim 1 or 2, wherein the backbone portion and the laterally extending platform further comprise at least one layer of a non-conductive material and a layer of electrically conductive material comprising at least one electrical channel on top of the non-conductive material or between multiple layers of a non-conductive material.

9. An implantable microelectrode comprising:
   a shank comprising a backbone and a laterally extending platform, the laterally extending platform having a thickness of between about 0.5 and 10 microns and less than the backbone and extending up to about 250 microns radially from the backbone,
   one or more electrode sites, and
   one or more conductive interconnects disposed between layers of dielectric in one or both of the backbone and the laterally extending platform, the dielectric layers insulating the interconnects on top and bottom sides, wherein the interconnects terminate with respective electrode sites and/or with bond pads and wherein at least one electrode site is disposed at least partially on or in the laterally extending platform.

10. The implantable microelectrode of claim 9, wherein the at least one electrode site disposed at least partially on or in the laterally extending platform comprises surface area disposed at least partially on or in the top, bottom, and/or most lateral sides of the laterally extending platform.

11. The implantable microelectrode of claim 9, further comprising:
   a plurality of interconnects disposed within the microelectrode between layers of dielectric material,
   a plurality of electrode sites, at least some of which are disposed on the laterally extending platform and which are in contact with a corresponding interconnect, and
   a plurality of bond pads, at least some of which are in contact with a respective interconnect, wherein at least one of the electrode sites is a recording site or a stimulation site.

* * * * *